US008586035B2

(12) United States Patent
Kopf et al.

(10) Patent No.: US 8,586,035 B2
(45) Date of Patent: Nov. 19, 2013

(54) USE OF IL-23 ANTAGONISTS FOR TREATMENT OF INFECTION

(75) Inventors: Manfred Kopf, Zurich (CH); Luigina Romani, Perugia (IT); Robert A. Kastelein, Portola Valley, CA (US); Alissa A. Chackerian, Sunnyvale, CA (US)

(73) Assignee: Merck Sharp & Dohme Corp., Rahway, NJ (US)

( * ) Notice: Subject to any disclaimer, the term of this patent is extended or adjusted under 35 U.S.C. 154(b) by 465 days.

(21) Appl. No.: 12/525,003

(22) PCT Filed: Feb. 8, 2008

(86) PCT No.: PCT/US2008/001717
§ 371 (c)(1),
(2), (4) Date: Apr. 30, 2010

(87) PCT Pub. No.: WO2008/153610
PCT Pub. Date: Dec. 18, 2008

(65) Prior Publication Data
US 2010/0291084 A1 Nov. 18, 2010

Related U.S. Application Data

(60) Provisional application No. 60/889,475, filed on Feb. 12, 2007.

(51) Int. Cl.
*A61K 39/00* (2006.01)
*A61K 39/395* (2006.01)

(52) U.S. Cl.
USPC .................. 424/130.1; 424/133.1; 424/135.1; 424/141.1; 424/143.1; 424/152.1

(58) Field of Classification Search
None
See application file for complete search history.

(56) References Cited

U.S. PATENT DOCUMENTS

| 4,144,346 | A | 3/1979 | Heeres et al. | |
|---|---|---|---|---|
| 4,223,036 | A | 9/1980 | Heeres et al. | |
| 4,267,179 | A | 5/1981 | Heeres et al. | |
| 4,404,216 | A | 9/1983 | Richardson | |
| 7,247,711 | B2 | 7/2007 | Benson et al. | |
| 7,252,971 | B2 | 8/2007 | Benson et al. | |
| 2003/0064069 | A1* | 4/2003 | Thompson et al. | 424/145.1 |
| 2005/0137385 | A1 | 6/2005 | Benson et al. | |
| 2005/0208052 | A1* | 9/2005 | Katsikis et al. | 424/145.1 |
| 2006/0193821 | A1 | 8/2006 | Diener et al. | |
| 2007/0009526 | A1* | 1/2007 | Benson et al. | 424/145.1 |
| 2009/0117126 | A1 | 5/2009 | Adams et al. | |
| 2009/0175881 | A1 | 7/2009 | Presta et al. | |

FOREIGN PATENT DOCUMENTS

| WO | WO 98/10782 | 3/1998 |
|---|---|---|
| WO | WO99-05280 | 2/1999 |
| WO | WO00-73451 | 12/2000 |
| WO | WO01/18051 | 3/2001 |
| WO | WO01-85790 | 11/2001 |
| WO | WO 2004/042009 | 5/2004 |
| WO | WO2004-101750 | 11/2004 |
| WO | WO2005-010044 | 2/2005 |
| WO | WO2005-058349 | 6/2005 |
| WO | WO2006-013107 | 2/2006 |
| WO | WO2006-109195 | 10/2006 |
| WO | WO2007-005955 | 1/2007 |
| WO | WO2007-024846 | 3/2007 |
| WO | WO2007-027714 | 3/2007 |
| WO | WO2007-076524 | 7/2007 |
| WO | WO2007-147019 | 12/2007 |
| WO | WO2008-103432 | 8/2008 |
| WO | WO2008-103473 | 8/2008 |
| WO | WO2008-106134 | 9/2008 |
| WO | WO2010-027767 | 3/2010 |

OTHER PUBLICATIONS

Becker et al. (2006) *J. Immunol.* 177(5):2760-2764, "Cutting edge: IL-23 cross-regulates IL-12 production in T cell-dependent experimental colitis".
Belladonna et al. (2006) *Cytokine* 34;161-169 "IL-23 neutralization protects mice from Gram-negative endotoxic shock".
Bettelli and Kuchroo (2005) *J. Exp. Med.* 201(2):169-171, "IL-12- and IL-23—induced T helper cell subsets: birds of the same feather flock together".
Bozza et al. (2005) *J. Immunol.* 174(5):2910-2918, "A crucial role for tryptophan catabolism at the host/*Candida albicans* interface".
Cenci et al. (1998) *J. Immunol.* 161(7):3543-3550, "IFN-gamma is required for IL-12 responsiveness in mice with *Candida albicans* infection".
Chackerian et al. (2006) *Infection and Immunity* 74(11):6092-6099, "Neutralization or absence of the Interleukin-23 pathway does not compromise immunity to mycobacterial infection".
Chen et al. (2006) *J. Clinical Investigation* 116(5):1317-1326, "Anti-IL-23 therapy inhibits multiple inflammatory pathways and ameliorates autoimmune encephalomyelitis".
Chensue et al. (1994) *Am. J. Pathol.* 145(5):1105-1113, "Cytokine responses during mycobacterial and schistosomal antigen-induced pulmonary granuloma formation. Production of Th1 and Th2 cytokines and relative contribution of tumor necrosis factor".
Cooper et al. (1993) *J. Exp. Med.* 178(6):2243-2247, "Disseminated tuberculosis in interferon gamma gene-disrupted mice".
Cooper (2007) *Eur. J. Immunol.* 37:2680-2682, "IL-23 and IL-17 have a multi-faceted largely negative role in fungal infection".
Cruz et al. (2006) *J. Immunol.* 177(3):1416-1420, "Cutting edge: IFN-gamma regulates the induction and expansion of IL-17-producing CD4 T cells during mycobacterial infection".
Elkins et al. (2002) *Infection Immunity* 70(4):1936-1948, "In vivo clearance of an intracellular bacterium, *Francisella tularensis* LVS, is dependent on the p40 subunit of Interleukin-12 (IL-12) but not on IL-12 p70".

(Continued)

*Primary Examiner* — Albert Navarro
(74) *Attorney, Agent, or Firm* — Gregory R. Bellomy

(57) ABSTRACT

Methods and compositions comprising antagonists of IL-23 are provided for the treatment of infections, such as chronic bacterial, viral and fungal infections.

12 Claims, 7 Drawing Sheets

(56) References Cited

OTHER PUBLICATIONS

Flynn et al. (1993) *J. Exp. Med.* 178(6):2249-2254, "An essential role for interferon gamma in resistance to *Mycobacterium tuberculosis* infection".
Frucht (2002) *Sci STKE 2002*, E1-E3, "IL-23: a cytokine that acts on memory T cells".
Gafa et al. (2006) *Infect. Immun.* 74(3):1480-1489, "Human Dendritic Cells following *Aspergillus fumigatus* Infection Express the CCR7 Receptor and a Differential Pattern of Interleukin-12 (IL-12), IL-23, and IL-27 Cytokines, Which Lead to a Th1 Response".
Han and Ulevitch (2005) *Nat. Immunol.* 6(12):1198-1205, "Limiting inflammatory responses during activation of innate immunity".
Happel et al. (2005) *J. Exp. Med.* 202(6):761-769, "Divergent roles of IL-23 and IL-12 in host defense against *Klebsieila pneumoniae*".
Happel et al. (2005) *Infect. Immun.* 73(9):5782-5788, "Pulmonary interleukin-23 gene delivery increases local T-cell immunity and controls growth of *Mycobacterium tuberculosis* in the lungs".
Harrington et al. (2006) *Curr. Opin. Immunol.* 18(3):349-356, "Expanding the effector CD4 T-cell repertoire: the Th17 lineage".
Hunter (2005) *Nat. Rev. Immunol.* 5:521-531, "New IL-12-family members: IL-23 and IL-27, cytokines with divergent functions".
Khader et al. (2005) *J. Immunol.* 175(2):788-795, "IL-23 compensates for the absence of IL-12p70 and is essential for the IL-17 response during tuberculosis but is dispensable for protection and antigen-specific IFN-gamma responses if IL-12p70 is available".
Kindler et al. (1989) *Cell* 56(5):731-740, "The inducing role of tumor necrosis factor in the development of bactericidal granulomas during BCG infection".
Kleinschek et al. (2006) *J. Immunol.* 176:1098-1106, "IL-23 enhances the inflammatory cell response in *Cryptococcus neoformans* infection and induces a cytokine pattern distinct from IL-12".
Kullberg et al. (2006) *J. Exp. Med.* 203(11):2485-2494, "IL-23 plays a key role in *Helicobacter hepaticus*-induced T cell-dependent colitis".
Langrish et al. (2004) *Immunol. Rev.* 202:96-105, "IL-12 and IL-23: master regulators of innate and adaptive immunity".
Langrish et al. (2005) *J. Exp. Med.* 201(2):233-240, "IL-23 drives a pathogenic T cell population that induces autoimmune inflammation".
Lilic (2002) *Curr. Opin. Infect. Dis.* 15(2):143-147, "New perspectives on the immunology of chronic mucocutaneous candidiasis".
Mangan et al. (2006) *Nature* 441(7090):231-234, "Transforming growth factor-beta induces development of the T(H)17 lineage)".
McKenzie et al. (2006) *Trends Immunol.* 27(1):17-23, "Understanding the IL-23-IL-17 immune pathway".
Mellor and Munn (2004) *Nat. Rev. Immunol.* 4(10):762-774, "IDO expression by dendritic cells: tolerance and tryptophan catabolism".
Mencacci et al. (1996) *Infect. Immun.* 64(12):4907-4914, "CD4+ T-helper-cell responses in mice with low-level *Candida albicans* infection".
Mencacci et al. (1998) *J. Immunol.* 161(11):6228-6237, "IL-10 is required for development of protective Th1 responses in IL-12-deficient mice upon *Candida albicans* infection".

Murphy et al. (2003) *J. Exp. Med.* 198(12):1951-1957, "Divergent Pro- and anti-inflammatory roles for IL-23 and IL-12 in joint autoimmune inflammation".
Oppmann et al. (2000) *Immunity* 13:715-725, "Novel p19 protein engages IL-12p40 to form a cytokine, IL-23, with biological activities similar as well as distinct from IL-12".
Parham et al. (2002) *J. Immunol.* 168:5699-5708, "A receptor for the heterodimeric cytokine IL-23 is composed of IL-12Rβ1 and a novel cytokine receptor subunit, IL-23R".
Park et al. (2005) *Nat. Immunol.* 6(11):1133-1141, "A distinct lineage of CD4 T cells regulates tissue inflammation by producing interleukin 17".
Romani et al. (1992) *J. Exp. Med.* 176(1):19-25, "Neutralizing antibody to interleukin 4 induces systemic protection and T helper type 1-associated immunity in murine candidiasis".
Romani (2004) *Nat. Rev. Immunol.* 4(1):1-23, "Immunity to fungal infections".
Romani and Puccetti (2006) *Trends Microbiol.* 14(4):183-189, "Protective tolerance to fungi: the role of IL-10 and tryptophan catabolism".
Rutitzky et al. (2005) *J. Immunol.* 175(6):3920-3926, "Severe CD4 T cell-mediated immunopathology in murine schistosomiasis is dependent on IL-12p40 and correlates with high levels of IL-17".
Ryan et al. (2005) *J. Allergy Clin. Immunol.* 116(5):1158-1159, "CD4+CD25+ T-regulatory cells are decreased in patients with autoimmune polyendocrinopathy candidiasis ectodermal dystrophy".
Sonderegger et al. (2006) *Eur. J. Immunol.* 36(11):2849-56, "Neutralization of IL-17 by active vaccination inhibits IL-23-dependent autoimmune myocarditis".
Vanden Eijnden et al. (2005) *Eur. J. Immunol.* 35(2):469-475, "IL-23 up-regulates IL-10 and induces IL-17 synthesis by polyclonally activated naive T cells in human".
Veldhoen et al. (2006) *Immunity* 24:179-189, "TGFβ in the context of an inflammatory cytokine milieu supports de novo differentiation of IL-17-producing T cells".
Wiekowski et al. (2001) *J. Immunol.* 166:7563-7570, "Ubiquitous transgenic expression of the IL-23 subunit p19 induces multiorgan inflammation, runting, infertility, and premature death".
Yen et al. (2006) *J. Clin. Invest.* 116(5):1310-1316, "IL-23 is essential for T cell-mediated colitis and promotes inflammation via IL-17 and IL-6".
Zelante et al. (2007) *Eur. J. Immunol.* 37:2695-2706, "IL-23 and the Th17 pathway promote inflammation and impair antifungal immune resistance".
Liming et al. (2006) *Int. J. Respiration* 26(4):283-285 "Interleukin 23 and Respiratory System Disease".
Jiawen et al. (2006) *China J. Leprosy Skin Dis.* 22(4):270-273 "The expression of IL-12 and IL-23 in mice with systemic *Candida*".
Aggarwal, et al., (2003) *J Biol. Chem.* 278(17):1910-1914 "Interleukin-23 promotes a distinct CD4 T cell activation state characterized by the production of Interleukin-17".
Huang, et al., (2004) *JID* 190:624-631 "Requirement of Interleukin-17A for systemic anti-*Candida albicans* host defense in mice".

\* cited by examiner

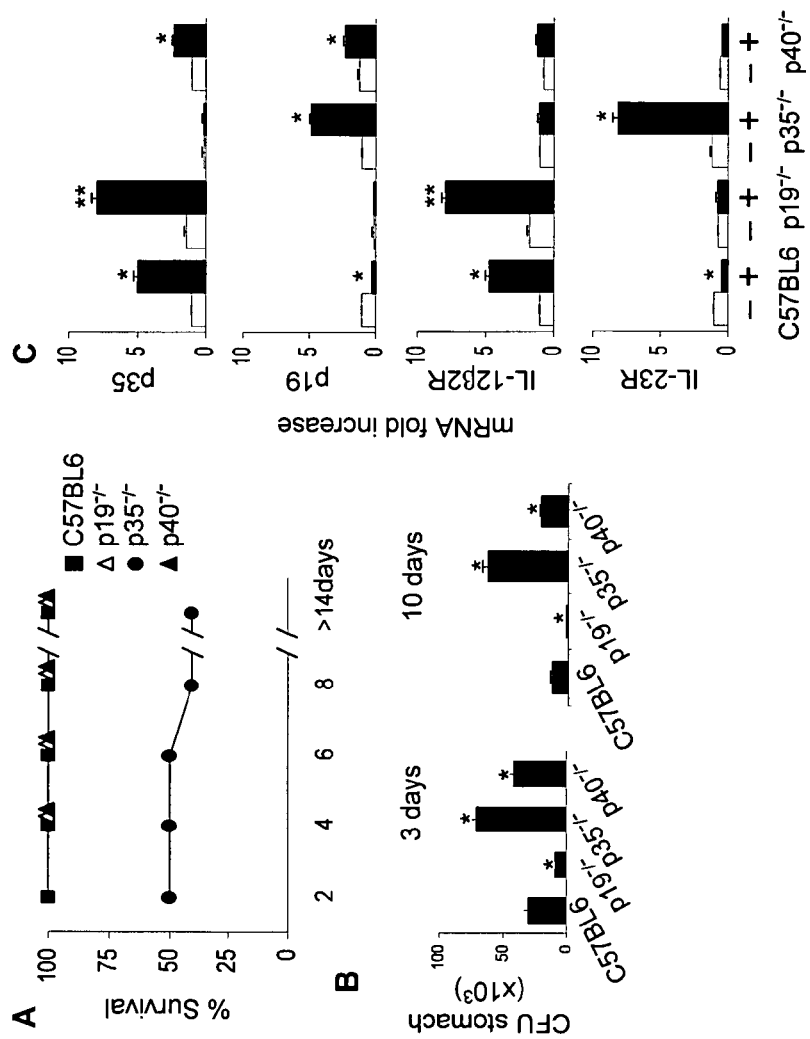
Fig. 1 A, B, C

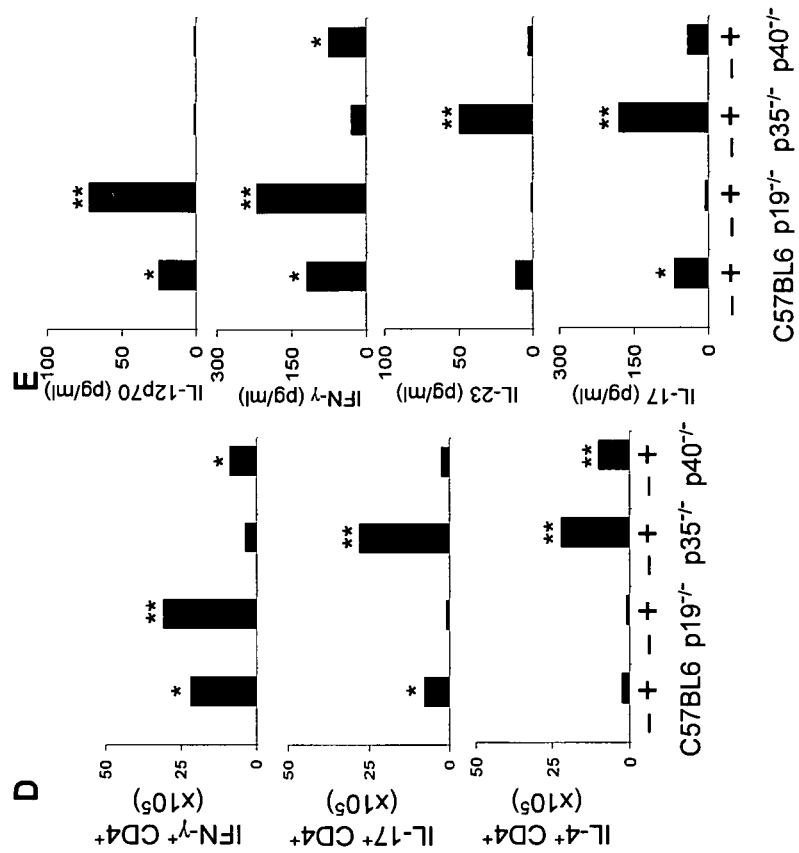
Fig. 1 D, E

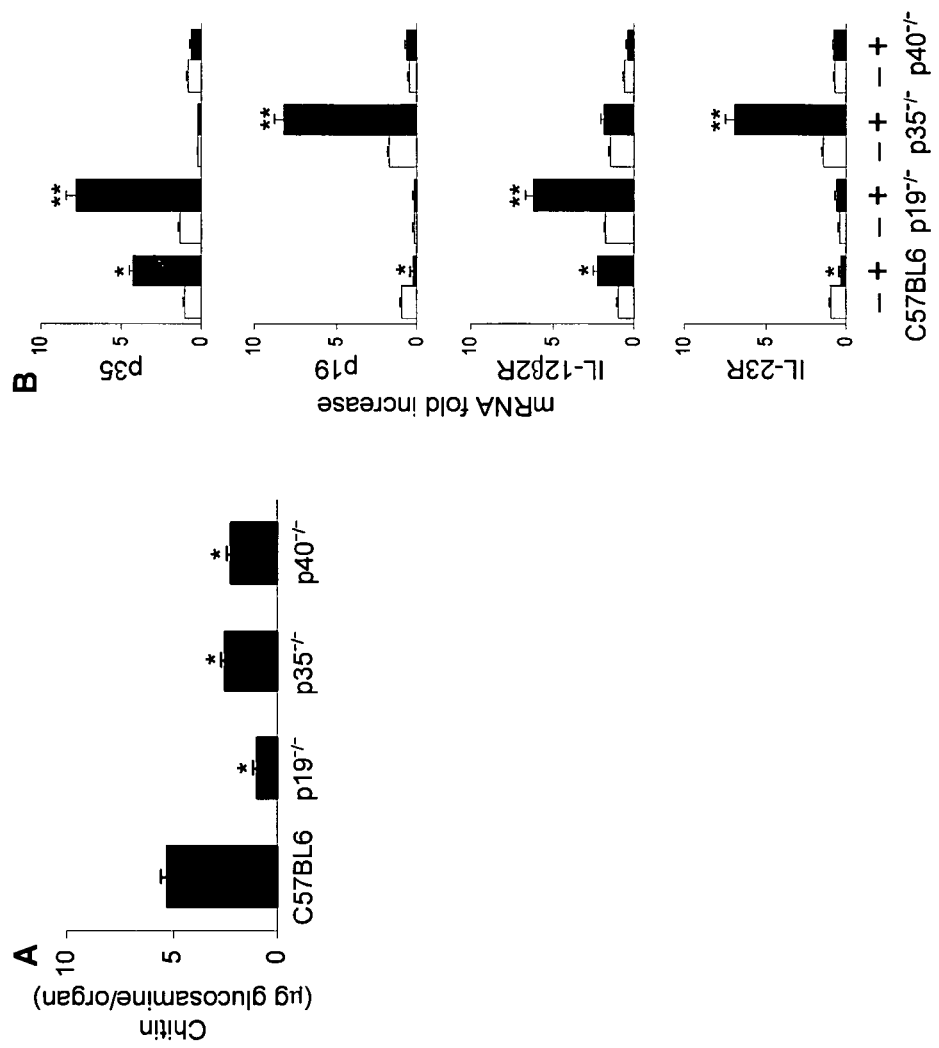
Fig. 2 A, B

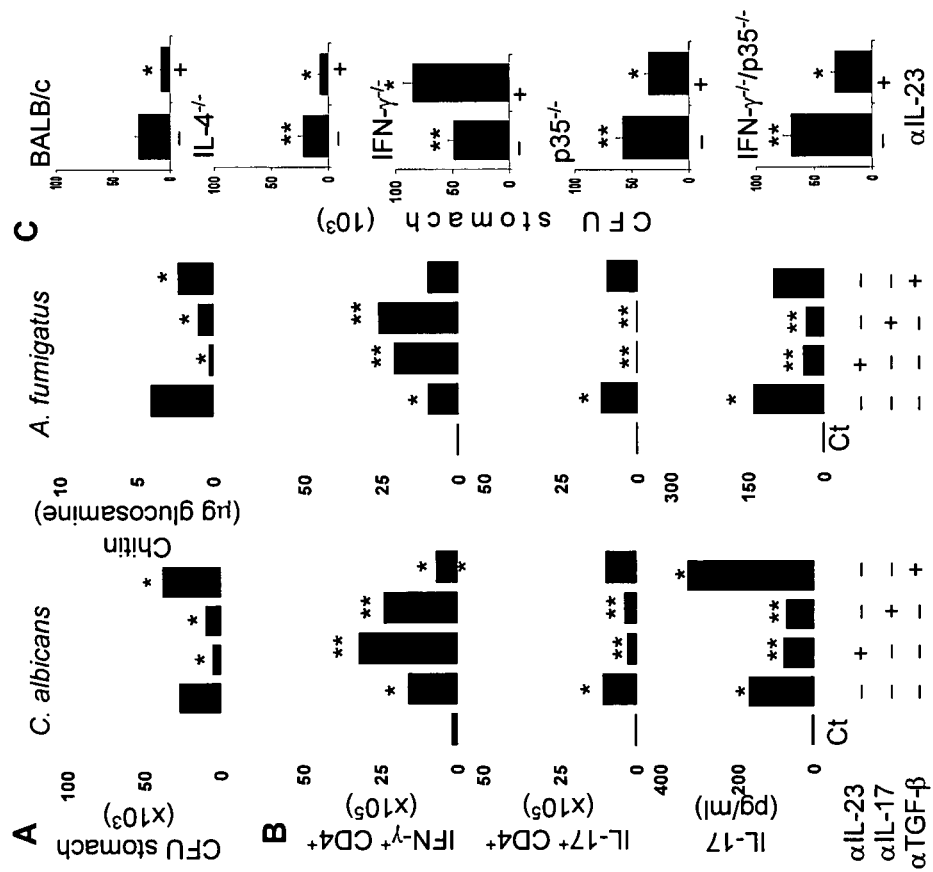
Fig. 3 A, B, C

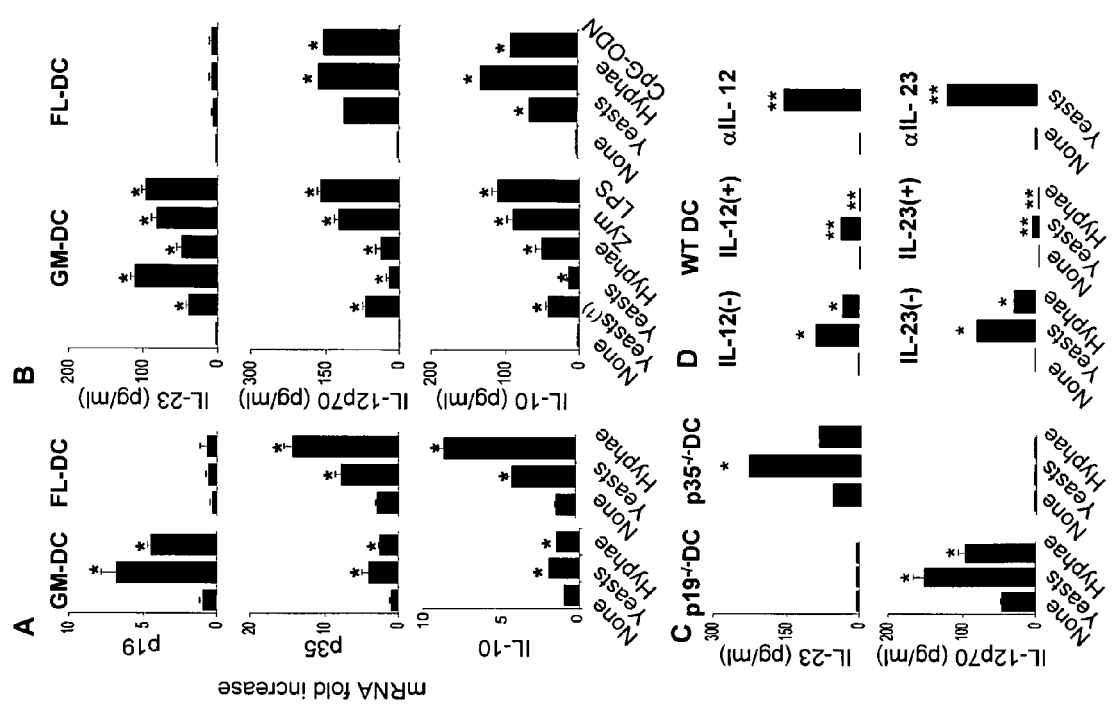
Fig. 4 A, B, C, D

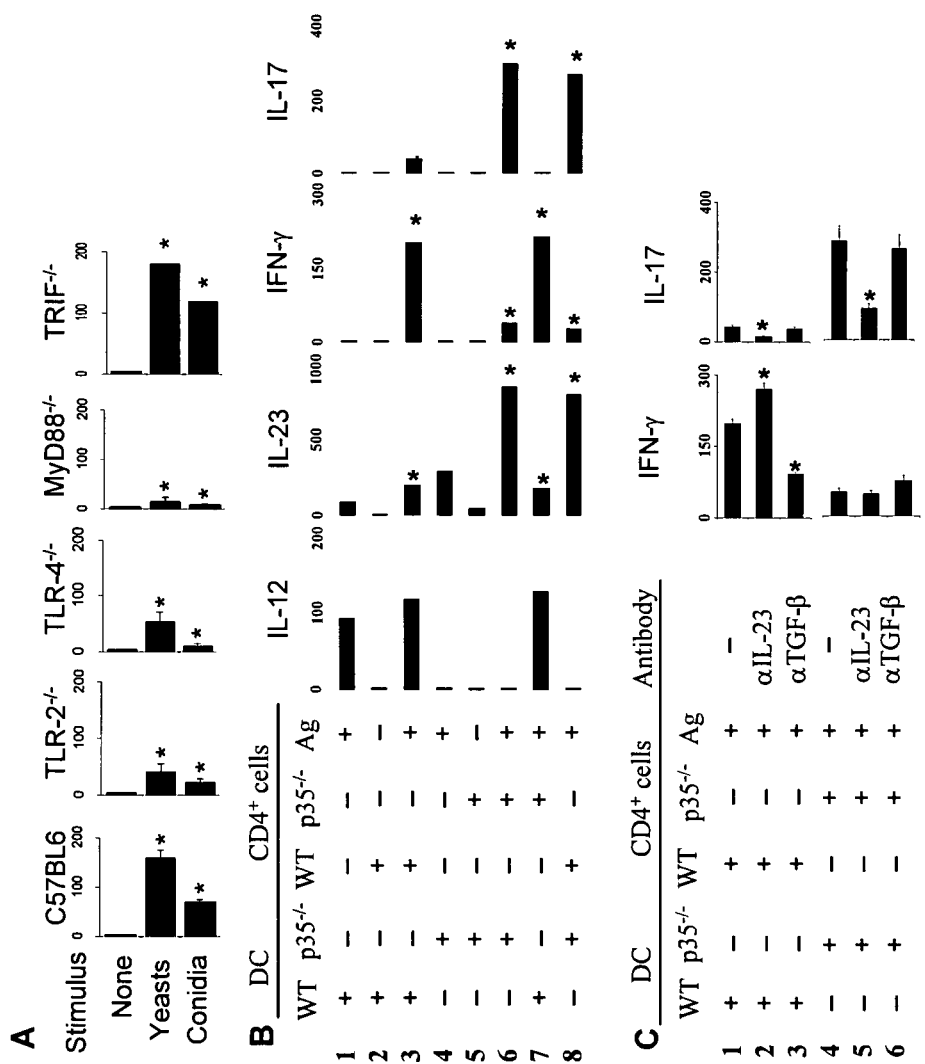
Fig. 5 A, B, C

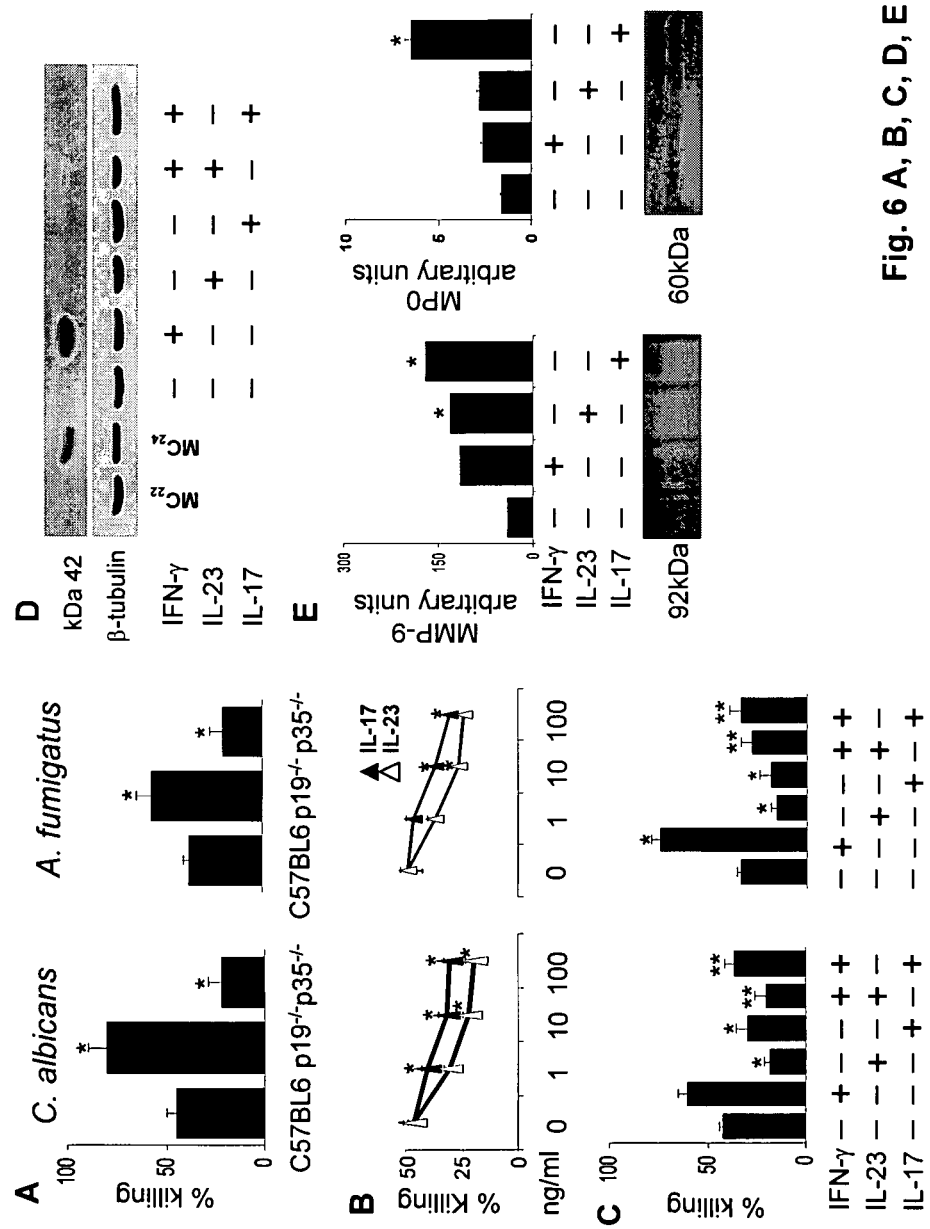
Fig. 6 A, B, C, D, E

USE OF IL-23 ANTAGONISTS FOR TREATMENT OF INFECTION

FIELD OF THE INVENTION

The present invention relates generally to treatment of infections. Specifically, the invention relates to administration of antagonist of IL-23, e.g. antibodies, to subjects exhibiting infections, such as chronic bacterial, fungal or viral infections.

BACKGROUND OF THE INVENTION

A number of pathogens cause chronic infections. Various viruses, fungi and bacteria, for example, can cause persistent infections that fail to resolve.

As the number of severe fungal infections continues to rise, the need for methods and compositions for their treatment is more urgent. Major fungal pathogens include *Candida albicans*, *Aspergillus fumigatus* and *Cryptococcus neoformans*, with estimated annual incidence for invasive mycoses involving these pathogens of 72-228 (for *Candida* species), 12-34 (for *Aspergillus* species) and 30-66 (for *C. neoformans*) infections per million population in the United States. Pfaller et al. (2006) *Clin. Infect. Dis.* 43:S3-14. The rise in fungal infections is primarily due to the increasing number of immuno-compromised patients as a result of medical advances (transplantation and chemotherapy), and as a result of the increasing population of AIDS patients. More than 80% of fungal infections in immunocompromised patients are caused by *Candida* species. Cryptococcosis is the second most prevalent fungal infection in AIDS patients following candidiasis. Aspergillosis is responsible for at least 30% of the infections in cancer and organ transplant patients and has a high mortality rate.

Although fluconazole has been an effective drug against fungal pathogens for a number of years, resistance is increasing. Alternatives such as amphotericin B have serious drawbacks, including such side effects as fever, kidney damage, anemia, low blood pressure, headache, nausea, vomiting and phlebitis.

Bacterial infections remain an important issue despite the prevalence of antibiotics, in light of an increased population of immune compromised individuals and a widespread development of antibiotic resistant bacterial strains. Immune compromised individuals include the elderly, transplant recipients, chemotherapy patients, and individuals with acquired immune deficiency syndrome (AIDS). Nearly two million patients in the United States get an infection in the hospital each year, and 70% of the bacteria responsible for those infections are resistant to at least one antibiotic. NIAID Fact Sheet, "The Problem of Antimicrobial Resistance," April 2006. In recent years, about 90,000 people in the United States die from infections, up from 13,300 in 1992. Although most bacterial infections remain susceptible to a prolonged course of therapy of at least one antibiotic (e.g. continuous intravenous administration of vancomycin), there is no guarantee that this will remain true with future pathogenic bacteria. Methicillin resistant *Stapholococcus aureus* (MRSA) is a prime example of a multiple-antibiotic-resistant microbe that represents a significant public health challenge. In 2002, the Centers for Disease Control (CDC) reported the first case of a *S. aureus* infection that was completely resistant to vancomycin (dubbed VRSA) in a patient in Michigan. Persistent bacterial pathogens also include *Salmonella* spp., *Brucella* spp. and *Chlamydia* spp.

Mycobacteria are a diverse and widely distributed group of aerobic, nonsportulating, nonmotile bacilli that have a high cell-wall lipid content and a slow growth rate. Members of the genus *Mycobacterium* vary in virulence, e.g., from harmless to species with significant pathogenicity, for example, *M. tuberculosis*, the causative agent in tuberculosis (TB). TB is the second leading infectious cause of death in the world. It is estimated that about two billion people, or one third of the world's population, are infected with *M. tuberculosis*. Eight million new cases and nearly three million deaths occur annually. TB is directly responsible for 7% of all deaths world wide, and the global epidemic is likely to worsen as a result of the spread of drug-resistant organisms and the ongoing HIV epidemic. See, e.g., Dale and Federman (eds.) (2002) *WebMD Scientific American Medicine*, WebMD Professional Publishing, New York, N.Y.

Most current methods to treat TB involve the use of broad spectrum anti-infective agents such as isoniazid, rifampin, pyrazinamide, ethambutol, streptomycin, ciprofloxacin, and ofloxacin. Such agents, however, can cause toxicities in various organs, and with the growth of several antibiotic resistant strains of TB, are losing efficaciousness. Reducing the mycobacterial burden in the lungs of tuberculosis patients with the use of a variety of non-antibiotic agents can prevent disease formation, transmission, and death.

Chronic viral infections also represent a significant threat to public health. Failure to completely eradicate viral infections such as hepatitis C virus (HCV) or human immunodeficiency virus (HIV) can lead to subsequent reactivations and complications such as liver cancer or acquired immune deficiency syndrome (AIDS), respectively. Robertson & Hasenkrug (2006) *Springer Semin. Immun.* 28:51. In addition, human papillomavirus (HPV) genotypes 16, 18, 31, 33, 45, and 56 account for more than 95% of cases of cervical cancer. Berzofsky et al. (2004) *J. Clin. Invest.* 114:450. It is estimated that chronic infections arise in virtually 100% of cases of HIV infection, 55-85% of cases of HCV infection, and over 30% of cases of HPV. Berzofsky et al. (2004).

The need exists for improved methods and compositions for treatment and/or prevention of bacterial, viral and fungal infections. Such methods and compositions are preferably less toxic and/or more efficacious that existing treatment methods and compositions.

SUMMARY OF THE INVENTION

The present invention meets these needs and more by providing compositions, medicaments and methods of using antagonists of IL-23 to combat bacterial, viral and fungal infections.

In one aspect the invention relates to methods of treatment of a subject having an infection, suspected of having an infection, or at risk of acquiring an infection, involving administration of an antagonist of IL-23. In one embodiment the antagonist is a binding compound, such as an antibody or binding fragment thereof, that binds to IL-23 or the p19 subunit thereof. In some embodiments the binding of the antibody blocks binding of IL-23 or its p19 subunit to the IL-23 receptor or the IL-23R subunit thereof. In another embodiment the antagonist of IL-23 binds to IL-23 receptor or the IL-23R subunit thereof. In some embodiments the antagonist that binds to IL-23 receptor, or the IL-23R subunit thereof, and blocks binding to IL-23 or the p19 subunit thereof. In another aspect the invention relates to compositions for use in said methods of treatment.

In some embodiments the infectious disorder comprises an infectious disease, such as a bacterial, mycobacterial, viral or fungal infection. In one embodiment the infectious disorder is a mycobacterial infection caused by *M. bovis, M, leprae,* or *M. tuberculosis.* In one embodiment the infectious disorder is TB. In another embodiment the infectious disorder is a fungal infection selected from the group consisting of onychomycosis, candidiasis, aspergillosis, cryptococcosis. In yet another embodiment the infectious disorder is a fungal infection caused by *C. albicans* (e.g. chronic mucocutaneous candidiasis, thrush), *C. neoformans* or *A. fumigatus.* In a further embodiment the infectious disorder is a viral infection, e.g. a viral infection caused by human immunodeficiency virus (HIV), hepatitis B virus (HBV), hepatitis C virus (HCV) or human papillomavirus (HPV).

In other embodiments, the infectious disorder is a chronic infection. In various embodiments the chronic infection has persisted, despite at least one previous attempt to resolve the infection, for 1, 2, 4, 6, 9, 12, 18, 24, 36 or 48 months or longer. In various embodiments the previous attempt to resolve the chronic infection involves treatment with antimicrobial agents, antibiotics, antiviral agents, or antifungal agents.

In one embodiment the invention relates to combination therapy combining administration of an antagonist of IL-23 with at least one other therapeutic modality, such as another therapeutic agent. In various embodiments, the other therapeutic agent is an IL-17A antagonist, an IL-17F antagonist, an IL-12 agonist (including IL-12), a TGF-β antagonist, or an IL-6 antagonist. In another embodiment the other therapeutic agent is one or more antifungal agent selected from the group consisting of posaconazole, fluconazole, voriconazole, itraconazole, ketoconazole, liarozole, irtemazol, clotrimazole, miconazole, econazole, butoconazole, oxiconazole, sulconazole, tioconazole, and terconazole, substituted thiazoles, thiadiazole, oxadiazole, caspofungin, amphotericin B, nystatin, pimaricin, flucytosine (5-fluorocytosine), naftifine, terbinafine, butenafine, thiocarbonate tolnaftate, griseofulvin, amiodarone, ciclopirox, sulbentine, amorolfine, clioquinol, gentian violet, potassium iodide, sodium thiosulfate, carbolfuchsin solution, and the echinocandins (e.g. caspofungin acetate, micafungin and anidulafungin).

In another embodiment the other therapeutic agent is one or more antimicrobial agent selected from the group consisting of isoniazid, rifampin, pyrazinamide, ethambutol, streptomycin, ciprofloxacin, vancomycin or ofloxacin.

In another embodiment the other therapeutic agent is one or more antiviral agent selected from the group consisting of abacavir, acyclovir, amantadine, amprenavir, delavirdine, didanosine, efavirenz, famciclovir, indinavir, an interferon alfa (IFN-α), ribavirin, lamivudine, nelfinavir, nevirapine, oseltamivir, penciclovir, ribavirin, ritonavir, saquinavir, stavudine, valacyclovir, zalcitabine, zanamivir, zidovudine (azidodeoxythymidine, AZT).

In one aspect the invention relates to methods of enhancing a type 1 (Th1) immune response in a subject having an infection or suspected of having an infection. In various embodiments, enhancement of the Th1 response is reflected by an increase in the percentage of CD4$^+$ T cells expressing IFN-γ, a decrease in the percentage of CD4$^+$ T cells expressing IL-17A, or both, when compared to the percentage of T cells prior to treatment with an antagonist of IL-23. In various embodiments the increase or decrease is 1.5-, 2-, 3-, 5-, 10-, 20-, 50-fold or more. In another aspect the invention relates to compositions for use in said methods of enhancing a Th1 response.

In various embodiments the other therapeutic agent is administered before, and/or concurrently with, and/or after administration of the antagonist of IL-23. In one embodiment, an antagonist of IL-17A is administered before and/or concurrently with the antagonist of IL-23. In another embodiment, an antimicrobial, antifungal or antiviral agent is administered concurrently with the antagonist of IL-23.

In another aspect the invention relates to methods of treatment of a subject having an infection, suspected of having an infection, or at risk of acquiring an infection, involving administration of antagonists of IL-17A and/or IL-17F, such as antagonistic antibodies to the cytokines themselves or to their respective receptors or receptor subunits.

In other embodiments the antagonist of IL-23 comprises a polynucleotide. In various embodiments the polynucleotide is an antisense polynucleotide (e.g. antisense RNA) or a small interfering RNA (siRNA). In one embodiment the polynucleotide antagonist of IL-23 is delivered in gene therapy vector, such as an adenovirus, lentivirus, retrovirus or adenoassociated virus vector. In another embodiment the polynucleotide antagonist of IL-23 is delivered as a therapeutic agent.

In yet another embodiment the antagonist of IL-23 comprises a soluble receptor polypeptide. In one embodiment the antagonist of IL-23 is a soluble fragment derived from the extracellular domain of IL-23R.

In various embodiments the antagonist of IL-23 is an antibody or antigen binding fragment thereof. In various embodiment the antibody or antigen binding fragment thereof comprises a polyclonal antibody, a monoclonal antibody, a humanized antibody, a fully human antibody; an antibody fragment (e.g. Fab, Fab', Fab'-SH, Fv, scFv, F(ab')$_2$, and a diabody). In other embodiments the antagonist comprises a peptide mimetic of an antibody. In still further embodiments the antibody or antigen binding fragment thereof is detectably labeled. In one embodiment, the antagonist of IL-23 is an antibody, or antigen binding fragment thereof, that exhibits reduced complement activation, antibody-dependent cellular cytotoxicity (ADCC), or both. In one embodiment the IL-23 antagonist antibody or fragment thereof with reduced effector function is an anti-IL-23 receptor (e.g. anti-IL-23R) antibody or fragment. In various embodiments the antibody with reduced effector function is an antibody fragment (e.g. Fab, Fab', Fab'-SH, Fv, scFv, F(ab')$_2$), an IgG4, or has altered glycosylation.

In one embodiment, the invention relates to treatment of an infection, e.g. a chronic fungal, bacterial or viral infection, by administering an effective amount of a bispecific antibody that binds specifically to any two proteins selected from the group consisting of IL-23p19, IL-23R, IL-17A, IL-17F, IL-17R, IL-17R, IL-6 and TGF-β. In one embodiment the proteins are human proteins.

In one embodiment the antagonist of IL-23 is specific for IL-23 (or its receptor) and does not antagonize IL-12 (or its receptor). In various embodiments antagonism is measured by an in vitro binding assay (e.g. an ELISA) or by a bioassay (e.g. BaF3 cell proliferation or promotion of Th17 cell production). In various embodiments the ratio of the IC50 for inhibition of binding of IL-12 to its receptor to the IC50 for inhibition of binding of IL-23 to its receptor (IC50$_{IL-12}$/IC50$_{IL-23}$) is 1.5, 2, 3, 4, 5, 7, 10, 15, 20, 50, 100 or more.

In one embodiment the methods and compositions of the present invention are used to treat TB, and the success of the treatment is measured by a reduction in bacterial burden. In various embodiments the mycobacterial burden is measured by a tuberculin test, a Mantoux test, or presence of mycobacterial DNA or RNA in a clinical sample.

In some embodiments of the present invention the subject having an infection has been previously treated for the infection with other methods or compositions. In one embodiment, the previous treatment was not effective in eliminating infection. In another embodiment the subject having an infection, suspected of having an infection, or at risk of acquiring an infection, is immunocompromised, e.g. as a result of AIDS, transplant or chemotherapy.

The invention further encompasses use of antagonists of IL-23 in the manufacture of a medicament for the treatment of one or more infectious diseases selected from the group consisting of a fungal infection, a persistent fungal infection, candidiasis, chronic mucocutaneous candidiasis (CMC), aspergillosis, cryptococcosis, a viral infection, a persistent viral infection, HIV infection, HBV infection, HCV infection, a persistent bacterial infection, mycobacterial infection, *M. tuberculosis* infection, *M. bovis* infection, and *M. leprae* infection. In some embodiments, the medicament may comprise one or more additional therapeutic agents. In other embodiments the medicament of the present invention may be used in conjunction with one or more other therapeutic agents.

BRIEF DESCRIPTION OF THE FIGURES

FIGS. 1A-1E show the results of experiments on the role of IL-23/IL-17-dependent pathway in susceptibility to candidiasis. Mice were injected intragastrically with $10^8$ virulent *Candida*. Results are pooled from 3 experiments (6 mice per group per experiment).

FIG. 1A shows percent (%) survival over time for $p19^{-/-}$, $p35^{-/-}$, $p40^{-/-}$ and C57BL/6(WT) mice.

FIG. 1B shows fungal growth (CFU) in the stomach three and ten days after the infection. Results were statistically different ($p<0.05$, indicated by *) for $p19^{-/-}$, $p35^{-/-}$, or $p40^{-/-}$ mice when compared with C57BL/6 mice at both three and ten day timepoints.

FIG. 1C shows p35 and p19 mRNA expression (one day after the infection) and IL-12β2R and IL-23R mRNA expression (three days after the infection) in MLN. mRNA expression was measured by real-time RT-PCR.

FIG. 1D shows the frequencies of IFN-γ-, IL-17- or IL-4-producing MLN CD4+ cells a week after the infection. The frequency of cytokine-producing cells was measured by ELISPOT assay, and values are the mean number of cytokine-producing cells (±SE) per $10^5$ cells.

FIG. 1E shows the levels of inflammatory cytokines (IL-17, IL-23, IFN-γ, IL-γ) in the stomach homogenates three days after the infection. Cytokines were measured by ELISA (pg/ml).

In FIGS. 1C-1E, differences were statistically significant ($p<0.05$) when comparing infected (+) to uninfected (−) mice (*), and when comparing $p19^{-/-}$ or $p35^{-/-}$ mice to C57BL/6 mice (**), as indicated in the figures.

FIGS. 2A and 2B show the results of experiments on the role of IL-23/IL-17-dependent pathway in susceptibility to aspergillosis. Mice were infected intranasally with $2\times10^7$ *Aspergillus* resting conidia. Results shown in FIGS. 2A and 2B are pooled from four experiments (six animals/group).

FIG. 2A shows fungal growth (chitin content, expressed as μg glucosamine/organ) in the lung three days after the infection. Differences were statistically significant ($p<0.05$) when comparing $p19^{-/-}$, $p35^{-/-}$ or $p40^{-/-}$ mice to C57BL/6 mice (*).

FIG. 2B shows p35/p19 mRNA expression (one day after the infection) and IL-12β2R/IL-23R mRNA expression (three days after the infection) in TLN. Messenger RNA expression was measured by RT-PCR. Differences were statistically significant ($P<0.05$) when comparing infected (+) to uninfected (−) mice (*), and when comparing $p19^{-/-}$ or $p35^{-/-}$ mice to C57BL/6 mice (**), as indicated in the figure.

FIGS. 3A-3C show the results of experiments on the importance of the IL-23/IL-17-dependent pathway in susceptibility to fungal infections. Mice were infected as in FIGS. 1 and 2, and treated with 200 μg of p19- or IL-17-neutralizing antibodies 5 h after the infection, or with 1 mg TGF-β neutralizing antibody 5 and 24 h after the infection.

FIG. 3A shows fungal growth in the stomach or lung of mice with candidiasis (*C. albicans*) or aspergillosis (*A. fumigatus*) three days after the infection. Differences were statistically significant ($p<0.05$) when comparing treated (+) to untreated (−) mice (*), as indicated in the figure.

FIG. 3B shows the frequencies of IFN-γ- or IL-17-producing CD4+ cells from MLN or TLN from mice with candidiasis or aspergillosis, respectively, as determined by ELISPOT assay. Values are the mean number of cytokine-producing cells (±SE) per $10^5$ cells. FIG. 3B further shows actual IL-17 production (one week after the infection) in culture supernatants of antigen-stimulated unfractionated MLN or TLN. Differences were statistically significant ($p<0.05$) when comparing infected to uninfected (Ct) mice (*), and when comparing treated (+) to untreated (−) mice (**), as indicated in the figure.

FIG. 3C shows fungal growth in the stomach of mice with candidiasis treated with p19 neutralizing antibodies as above, three days after the infection. Differences were statistically significant ($p<0.05$) when comparing treated (+) to untreated (−) mice (*), and when comparing IL-$4^{-/-}$, IFN-$\gamma^{-/-}$, $p35^{-/-}$ or IFN-$\gamma^{-/-}$/$p35^{-/-}$ mice to BALB/c mice (**), as indicated in the figure.

FIGS. 4A-4D show the results of experiments on IL-23 and IL-12 production in DC subsets in response to fungi. Bone marrow DC obtained in the presence of GM-CSF+IL-4 (GM-DC) or FLT3-L (FL-DC) were stimulated with fungi and assessed for cytokine expression.

FIG. 4A shows real time RT-PCR analysis of cytokine mRNA expression, and FIG. 4B shows cytokine expression as measured by ELISA (pg/ml). Zymosan, LPS (10 μg/ml) or CpG-ODN 2006 (0.06 μM) were used as positive controls. DC were exposed to yeasts at 10:1 ratio. Differences were statistically significant ($p<0.05$) when comparing exposed to unexposed ("None") DC (*), as indicated in the figure.

FIG. 4C shows IL-12 and IL-23 production in splenic CD11c+DC from $p19^{-/-}$ or $p35^{-/-}$ mice. Mice were stimulated with fungi before the measurement of cytokines in culture supernatants.

FIG. 4D shows IL-12 and IL-23 production in splenic CD11c+DC from C57BL/6 mice exposed to fungi for 12 h in the presence (+) or absence (−) of IL-12 or IL-23 (10 ng/ml), or in the presence of neutralizing anti-IL-12 or anti-IL-23 antibodies (10 μg/ml), as indicated in the figure.

FIGS. 5A-5C show the results of experiments on IL-23 production by inflammatory DC in response to fungi, and specifically whether such production is TLR- and T cell-dependent.

FIG. 5A shows IL-23 production (pg/ml) in splenic CD11c+DC from different types of mice exposed to fungi 12 h earlier. Pooled results from four experiments are shown. Differences were statistically significant ($p<0.05$) when comparing exposed to unexposed ("None") DC (*), as indicated in the figure.

FIG. 5B shows expression of cytokines in various cell cultures and co-cultures. Splenic CD4+ T cells from C57BL/6 (WT) or $p35^{-/-}$ mice were cultured in the presence of the corresponding splenic DC either unpulsed (groups 2 and 5) or pulsed with *Candida* yeasts (Ag) (groups 3 and 6). Cytokines (IL-12, IL-23, IFN-γ, IL-17) were measured by ELISA five days post-pulse. Groups 1 and 4 are C57BL/6 or p35$^{-/-}$ DC stimulated with fungi and no T cells. Groups 7 and 8 are p35$^{-/-}$ or C57BL/6 CD4+ T cells cultivated with C57BL/6 or p35$^{-/-}$ DC, respectively, in the presence of the fungus. Differences are statistically significant (p<0.05, indicated by *) when groups 3 and 7 are compared to group 1 for IFN-γ production, and when groups 6 and 8 are compared to group 4 for IL-23 and IL-17 production, as indicated in the figure.

FIG. 5C shows data similar to those shown in FIG. 5B, except that some of the samples include anti-IL-23 or anti-TGF-β antibodies. Splenic CD4+ T cells from C57BL/6 (WT) (groups 1-3) or p35$^{-/-}$ (groups 4-6) mice were cultured in the presence of the corresponding splenic DC. Cultures were pulsed with *Candida* yeasts (Ag) for 5 days in the presence of 10 µg/ml of IL-23 or TGF-β neutralizing antibodies, and cytokines (IFN-γ, IL-17) were quantified in culture supernatants by ELISA. Differences are statistically significant (p<0.05, indicated by *) when groups 2 and 3 are compared to group 1 for IFN-γ and IL-17 production, and when group 5 is compared to group 4 for IL-17 production, as indicated in the figure.

FIGS. 6A-6E show the results of experiments on the ability of IL-23 and IL-17 to impair antifungal effector functions and subvert the anti-inflammatory program of PMN.

FIG. 6A shows fungicidal activity in PMN from C57BL/6 (WT), p19$^{-/-}$ or p35$^{-/-}$ mice after incubation with unopsonized yeasts (30 min) or conidia (60 min) at an effector to fungal cell ratio of 5:1, at 37° C. Results are plotted as the percentage of colony forming units inhibition (mean±SE). Results reflect pooled data from three experiments. Differences were statistically significant (p<0.05) when comparing p19$^{-/-}$ or p35$^{-/-}$ PMN to C57BL/6 (WT) PMN (*), as indicated in the figure.

FIG. 6B shows fungicidal activity of PMN from C57BL/6 (WT) mice exposed to IL-23 or IL-17 at the indicated concentrations. Differences were statistically significant (p<0.05) when comparing cytokine-exposed PMN to unexposed PMN (*).

FIGS. 6C and 6D shows fungicidal activity of PMN from C57BL/6 (WT) mice exposed to various combinations of IFN-γ (50 ng/ml), IL-23 (100 ng/ml) and IL-17 (100 ng/ml) for 60 min. Fungicidal activity was measured against *Candida* yeasts or *Aspergillus* conidia (FIG. 6C). MMP9/MPO production was also measured (FIG. 6D). Production of gelatinase and myeloperoxidase was assessed by gelatin zymography and Western blot analysis was performed on culture supernatants. Gels show bands corresponding to the active 92 kDa MMP9 and the 60 kDa MPO. Differences were statistically significant (p<0.05) when comparing cytokine-exposed PMN to unexposed PMN (*), and when comparing (IFN-γ+IL-23)- or (IFN-γ+IL-17)-exposed PMN to IFN-γ-exposed PMN (**), as indicated in the figure.

FIG. 6E shows bands on a Western blot. PMN were exposed in vitro to various combinations of IFN-γ, IL-23 and IL-17 for 12 h. IDO protein expression was then determined by Western Blotting. IDO-expressing MC$_{24}$ transfectants and mock-transfected MC$_{22}$ cells served as positive and negative controls, respectively. β-tubulin serves as a loading control.

DETAILED DESCRIPTION

As used herein, including the appended claims, the singular forms of words such as "a," "an," and "the," include their corresponding plural references unless the context clearly dictates otherwise. Unless otherwise indicated, exemplary embodiments provided herein are not to be considered to limit the scope of the invention. Such exemplary embodiments may be preceded by such phrases as "e.g.," "for example," "in one embodiment" or other such non-limiting language, or their exemplary nature may be apparent from the context (e.g. the "Examples"). Unless indicated otherwise, terms such a "does not inhibit" are intended to be relative rather than absolute. For example, an agent that inhibits IL-23 but "does not" inhibit IL-12 refers to an agent that is less effective at inhibiting IL-12 than IL-23 when the agent is present at a given concentration in comparable assays for the two cytokines.

All references cited herein are incorporated by reference in their entireties to the same extent as if each individual publication, database entry, patent application, or patent, was specifically and individually incorporated by reference.

I. Definitions

"Activation," "stimulation," and "treatment," as it applies to cells or to receptors, may have the same meaning, e.g., activation, stimulation, or treatment of a cell or receptor with a ligand, unless indicated otherwise by the context or explicitly. "Ligand" encompasses natural and synthetic ligands, e.g., cytokines, cytokine variants, analogues, muteins, and binding compositions derived from antibodies. "Ligand" also encompasses small molecules, e.g., peptide mimetics of cytokines and peptide mimetics of antibodies.

"Activation" can refer to cell activation as regulated by internal mechanisms as well as by external or environmental factors. "Response," e.g., of a cell, tissue, organ, or organism, encompasses a change in biochemical or physiological behavior, e.g., concentration, density, adhesion, or migration within a biological compartment, rate of gene expression, or state of differentiation, where the change is correlated with activation, stimulation, or treatment, or with internal mechanisms such as genetic programming.

"Activity" of a molecule may describe or refer to the binding of the molecule to a ligand or to a receptor, to catalytic activity; to the ability to stimulate gene expression or cell signaling, differentiation, or maturation; to antigenic activity, to the modulation of activities of other molecules, and the like. "Activity" of a molecule may also refer to activity in modulating or maintaining cell-to-cell interactions, e.g., adhesion, or activity in maintaining a structure of a cell, e.g., cell membranes or cytoskeleton. "Activity" can also mean specific activity, e.g., [catalytic activity]/[mg protein], or [immunological activity]/[mg protein], concentration in a biological compartment, or the like. "Proliferative activity" encompasses an activity that promotes, that is necessary for, or that is specifically associated with, e.g., normal cell division, as well as cancer, tumors, dysplasia, cell transformation, metastasis, and angiogenesis.

"Administration" and "treatment," as it applies to an animal, human, experimental subject, cell, tissue, organ, or biological fluid, refers to contact of an exogenous pharmaceutical, therapeutic, diagnostic agent, or composition to the animal, human, subject, cell, tissue, organ, or biological fluid. "Administration" and "treatment" can refer, e.g., to therapeutic, pharmacokinetic, diagnostic, research, and experimental methods. Treatment of a cell encompasses contact of a reagent to the cell, as well as contact of a reagent to a fluid, where the fluid is in contact with the cell. "Administration" and "treatment" also means in vitro and ex vivo treatments, e.g., of a cell, by a reagent, diagnostic, binding composition, or by another cell. "Treatment," as it applies to a human, veterinary, or research subject, refers to therapeutic treatment, prophylactic or preventative measures, to research and diagnostic applications. "Treatment" as it applies to a human, veterinary, or research subject, or cell, tissue, or organ, encompasses contact of IL-23 or IL-23R antagonist to a human or animal subject, a cell, tissue, physiological compartment, or physiological fluid. "Treatment of a cell" also encompasses situations where the IL-23 or IL-23R antagonist contacts IL-23R complex (IL-23R/IL-12Rbetal heterodimer), e.g., in the fluid phase or colloidal phase, but also situations where the antagonist does not contact the cell or the receptor.

"Binding composition" refers to a molecule, small molecule, macromolecule, antibody, a fragment or analogue thereof, or soluble receptor, capable of binding to a target. "Binding composition" also may refer to a complex of molecules, e.g., a non-covalent complex, to an ionized molecule, and to a covalently or non-covalently modified molecule, e.g., modified by phosphorylation, acylation, cross-linking, cyclization, or limited cleavage, which is capable of binding to a target. "Binding composition" may also refer to a molecule in combination with a stabilizer, excipient, salt, buffer, solvent, or additive, capable of binding to a target. "Binding" may be defined as an association of the binding composition with a target where the association results in reduction in the normal Brownian motion of the binding composition, in cases where the binding composition can be dissolved or suspended in solution.

The binding compounds of the invention may comprise bispecific antibodies. As used herein, the term "bispecific antibody" refers to an antibody, typically a monoclonal antibody, having binding specificities for at least two different antigenic epitopes. In one embodiment, the epitopes are from the same antigen. In another embodiment, the epitopes are from two different antigens. Methods for making bispecific antibodies are known in the art. For example, bispecific antibodies can be produced recombinantly using the co-expression of two immunoglobulin heavy chain/light chain pairs. See, e.g., Milstein et al. (1983) Nature 305: 537-39. Alternatively, bispecific antibodies can be prepared using chemical linkage. See, e.g., Brennan, et al. (1985) Science 229: 81. Bispecific antibodies include bispecific antibody fragments. See, e.g., Holliger, et al. (1993) Proc. Natl. Acad. Sci. U.S.A. 90: 6444-48, Gruber, et al., J. Immunol. 152: 5368 (1994).

A "classical TH1-type T cell" is a T cell that expresses interferon-gamma (IFNγ) to an extent greater than expression of each of IL-4, IL-5, or IL-13, while a "classical TH2-type T cell" is a T cell that expresses IL-4, IL-5, or IL-13, each to an extent greater than expression of IFNγ. "Extent" is typically 4-fold or more, more typically 8-fold or more, and most typically 16-fold or more than for a classical TH2-type cell.

"Memory T cells" as defined herein are a subset of long-lived T cells with prior exposure to a given antigen. Memory T cells can be present in an organism for years, allowing a rapid response to subsequent challenges by the same antigen. The phenotype for mouse memory T cells is defined as $CD4+^{high}CD45RB^{low}$. The phenotype of human memory T cells is defined as $CD45RA^{neg/low}CD45R0^{high}$. IL-23 treatment of these memory T cells results in proliferation and expression of IL-17. Unless otherwise indicated "IL-17," as used herein, refers to IL-17A. See, e.g., Moseley et al. (2003) Cytokine & Growth Factor Rev. 14:155.

"Conservatively modified variants" applies to both amino acid and nucleic acid sequences. With respect to particular nucleic acid sequences, conservatively modified variants refers to those nucleic acids that encode identical or essentially identical amino acid sequences or, where the nucleic acid does not encode an amino acid sequence, to essentially identical nucleic acid sequences. Because of the degeneracy of the genetic code, a large number of functionally identical nucleic acids may encode any given protein.

As to amino acid sequences, one of skill will recognize that an change in a nucleic acid, peptide, polypeptide, or protein sequence that substitutes an amino acid or a small percentage of amino acids in the encoded sequence for a conserved amino acid is a "conservatively modified variant." Conservative substitution tables providing functionally similar amino acids are well known in the art. An example of a conservative substitution is the exchange of an amino acid in one of the following groups for another amino acid of the same group (U.S. Pat. No. 5,767,063 issued to Lee, et al.; Kyte and Doolittle (1982) J. Mol. Biol. 157: 105-132):
(1) Hydrophobic: Norleucine, Ile, Val, Leu, Phe, Cys, or Met;
(2) Neutral hydrophilic: Cys, Ser, Thr;
(3) Acidic: Asp, Glu;
(4) Basic: Asn, Gln, H is, Lys, Arg;
(5) Residues that influence chain orientation: Gly, Pro;
(6) Aromatic: Trp, Tyr, Phe;
(7) Small amino acids: Gly, Ala, Ser.

"Effective amount" encompasses an amount sufficient to ameliorate or prevent a symptom or sign of the medical condition. Effective amount also means an amount sufficient to allow or facilitate diagnosis. An effective amount for a particular patient or veterinary subject may vary depending on factors such as the condition being treated, the overall health of the patient, the method route and dose of administration and the severity of side effects. See, e.g., U.S. Pat. No. 5,888,530. An effective amount can be the maximal dose or dosing protocol that avoids significant side effects or toxic effects. The effect will result in an improvement of a diagnostic measure or parameter by at least 5%, usually by at least 10%, more usually at least 20%, most usually at least 30%, preferably at least 40%, more preferably at least 50%, most preferably at least 60%, ideally at least 70%, more ideally at least 80%, and most ideally at least 90%, where 100% is defined as the diagnostic parameter shown by a normal subject. See, e.g., Maynard, et al. (1996) A Handbook of SOPs for Good Clinical Practice, Interpharm Press, Boca Raton, Fla.; Dent (2001) Good Laboratory and Good Clinical Practice, Urch Publ., London, UK.

"Exogenous" refers to substances that are produced outside an organism, cell, or human body, depending on the context. "Endogenous" refers to substances that are produced within a cell, organism, or human body, depending on the context.

"Infectious disease" refers to microbial, e.g., bacterial, viral, and/or fungal, infections of an organism, organ, tissue, or cell.

An "IL-17-producing cell" means a T cell that is not a classical TH1-type T cell or classical TH2-type T cell. "IL-17-producing cell" also means a T cell that expresses a gene or polypeptide (e.g., mitogen responsive P-protein; chemokine ligand 2; interleukin-17 (IL-17); transcription factor ROR-γT related; suppressor of cytokine signaling 3. etc.), where expression with treatment by an IL-23 agonist is greater than treatment with an IL-12 agonist, where "greater than" is defined as follows. Expression with an IL-23 agonist is ordinarily at least 5-fold greater, typically at least 10-fold greater, more typically at least 15-fold greater, most typically at least 20-fold greater, preferably at least 25-fold greater, and most preferably at least 30-fold greater, than with IL-12 treatment. Expression can be measured, e.g., with treatment of a population of substantially pure IL-17 producing cells.

Moreover, "IL-17-producing cell" includes a progenitor or precursor cell that is committed, in a pathway of cell development or cell differentiation, to differentiating into an IL-17-producing cell, as defined above. A progenitor or precursor cell to the IL-17 producing cell can be found in a draining lymph node (DLN). Additionally, "IL-17-producing cell" encompasses an IL-17-producing cell, as defined above, that has been, e.g., activated, e.g., by a phorbol ester, ionophore, and/or carcinogen, further differentiated, stored, frozen, desiccated, inactivated, partially degraded, e.g., by apoptosis, proteolysis, or lipid oxidation, or modified, e.g., by recombinant technology.

"Inhibitors" and "antagonists" refer to inhibitory molecules for the inhibition of, e.g., a ligand, receptor, cofactor, a gene, cell, tissue, or organ. A modulator of a gene, a receptor, a ligand, or a cell, is a molecule that alters an activity of the gene, receptor, ligand, or cell, where activity can be activated, inhibited, or altered in its regulatory properties. The modulator may act alone, or it may use a cofactor, e.g., a protein, metal ion, or small molecule. Inhibitors are compounds that decrease, block, prevent, delay activation, inactivate, desensitize, or down regulate, e.g., a gene, protein, ligand, receptor, or cell. Activators are compounds that increase, activate, facilitate, enhance activation, sensitize, or up regulate, e.g., a gene, protein, ligand, receptor, or cell. An inhibitor may also be defined as a composition that reduces, blocks, or inactivates a constitutive activity. An "antagonist" is a compound that opposes the actions of an agonist. An antagonist prevents, reduces, inhibits, or neutralizes the activity of an agonist. An antagonist can also prevent, inhibit, or reduce constitutive activity of a target, e.g., a target receptor, even where there is no identified agonist.

An antagonist of IL-23, for example, includes any agent that disrupts the biological activity of IL-23, such as amplification and survival of Th17 cells as described in greater detail infra. Antagonists of IL-23 receptor and IL-23R are subsets of antagonists of IL-23 because they serve to block the activity of IL-23 by blocking IL-23 signaling.

To examine the extent of inhibition, for example, samples or assays comprising a given protein, gene, cell, or organism, are treated with a potential activator or inhibitor and are compared to control samples without the inhibitor. Control samples, i.e., not treated with antagonist, are assigned a relative activity value of 100%. Inhibition is achieved when the activity value relative to the control is about 90% or less, typically 85% or less, more typically 80% or less, most typically 75% or less, generally 70% or less, more generally 65% or less, most generally 60% or less, typically 55% or less, usually 50% or less, more usually 45% or less, most usually 40% or less, preferably 35% or less, more preferably 30% or less, still more preferably 25% or less, and most preferably less than 25%. Activation is achieved when the activity value relative to the control is about 110%, generally at least 120%, more generally at least 140%, more generally at least 160%, often at least 180%, more often at least 2-fold, most often at least 2.5-fold, usually at least 5-fold, more usually at least 10-fold, preferably at least 20-fold, more preferably at least 40-fold, and most preferably over 40-fold higher.

Endpoints in activation or inhibition can be monitored as follows. Activation, inhibition, and response to treatment, e.g., of a cell, physiological fluid, tissue, organ, and animal or human subject, can be monitored by an endpoint. The endpoint may comprise a predetermined quantity or percentage of, e.g., an indicium of reduced bacterial burden, oncogenicity, or cell degranulation or secretion, such as the release of a cytokine, toxic oxygen, or a protease. The endpoint may comprise, e.g., a predetermined quantity of ion flux or transport; cell migration; cell adhesion; cell proliferation; potential for metastasis; cell differentiation; and change in phenotype, e.g., change in expression of gene relating to inflammation, apoptosis, transformation, cell cycle, or metastasis. See, e.g., Knight (2000) *Ann. Clin. Lab. Sci.* 30:145-158; Hood and Cheresh (2002) *Nature Rev. Cancer* 2:91-100; Timme et al. (2003) *Curr. Drug Targets* 4:251-261; Robbins and Itzkowitz (2002) *Med. Clin. North Am.* 86:1467-1495; Grady and Markowitz (2002) *Annu. Rev. Genomics Hum. Genet.* 3:101-128; Bauer et al. (2001) *Glia* 36:235-243; Stanimirovic and Satoh (2000) *Brain Pathol.* 10:113-126.

An endpoint of inhibition is generally 75% of the control or less, preferably 50% of the control or less, more preferably 25% of the control or less, and most preferably 10% of the control or less. Generally, an endpoint of activation is at least 150% the control, preferably at least two times the control, more preferably at least four times the control, and most preferably at least 10 times the control.

"Knockout" (KO) refers to the partial or complete reduction of expression of at least a portion of a polypeptide encoded by a gene, e.g., encoding a subunit of IL-23 or IL-23 receptor, where the gene is endogenous to a single cell, selected cells, or all of the cells of a mammal. KO also encompasses embodiments where biological function is reduced, but where expression is not necessarily reduced, e.g., a polypeptide that contains an inserted inactivating peptide. Disruptions in a coding sequence or a regulatory sequence are encompassed by the knockout technique. The cell or mammal may be a "heterozygous knockout", where one allele of the endogenous gene has been disrupted. Alternatively, the cell or mammal may be a "homozygous knockout" where both alleles of the endogenous gene have been disrupted. "Homozygous knockout" is not intended to limit the disruption of both alleles to identical techniques or to identical outcomes at the genome.

A composition that is "labeled" is detectable, either directly or indirectly, by spectroscopic, photochemical, biochemical, immunochemical, isotopic, or chemical methods. For example, useful labels include $^{32}$P, $^{33}$P, $^{35}$S, $^{14}$C, $^{3}$H, $^{125}$I, stable isotopes, fluorescent dyes, electron-dense reagents, substrates, epitope tags, or enzymes, e.g., as used in enzyme-linked immunoassays, or fluorettes. See, e.g., Rozinov and Nolan (1998) *Chem. Biol.* 5:713-728.

"Ligand" refers, e.g., to a small molecule, peptide, polypeptide, and membrane associated or membrane-bound molecule, or complex thereof, that can act as an agonist or antagonist of a receptor. "Ligand" also encompasses an agent that is not an agonist or antagonist, but that can bind to the receptor. Moreover, "ligand" includes a membrane-bound ligand that has been changed, e.g., by chemical or recombinant methods, to a soluble version of the membrane-bound ligand. By convention, where a ligand is membrane-bound on a first cell, the receptor usually occurs on a second cell. The second cell may have the same or a different identity as the first cell. A ligand or receptor may be entirely intracellular, that is, it may reside in the cytosol, nucleus, or some other intracellular compartment. The ligand or receptor may change its location, e.g., from an intracellular compartment to the outer face of the plasma membrane. The complex of a ligand and receptor is termed a "ligand receptor complex." Where a ligand and receptor are involved in a signaling pathway, the ligand occurs at an upstream position and the receptor occurs at a downstream position of the signaling pathway.

A "marker" relates to the phenotype of a cell, tissue, organ, animal, e.g., of an IL-17 producing cell. Markers are used to detect cells, e.g., during cell purification, quantitation, migration, activation, maturation, or development, and may be used for both in vitro and in vivo studies. An activation marker is a marker that is associated with cell activation.

"Purified cell" encompasses, e.g., one or more "IL-17 producing cells" that is substantially free of other types of cells, e.g., contamination by other types of T cells. Purity can be assessed by use of a volume that is defined by geometric coordinates or by a compartment comprising, e.g., a flask, tube, or vial. A "purified IL-17 producing cell" can be defined by, e.g., a compartment where the "IL-17 producing cells" normally constitute at least 20% of all the cells, more normally at least 30% of all the cells, most normally at least 40% of all the cells, generally at least 50% of all the cells, more generally at least 60% of all the cells, most generally at least 70% of all the cells, preferably at least 80% of all the cells, more preferably at least 90% of all the cells; and most preferably at least 95% of all the cells.

"Small molecule" is defined as a molecule with a molecular weight that is less than 10 kD, typically less than 2 kD, and preferably less than 1 kD. Small molecules include, but are not limited to, inorganic molecules, organic molecules, organic molecules containing an inorganic component, molecules comprising a radioactive atom, synthetic molecules, peptide mimetics, and antibody mimetics. As a therapeutic, a small molecule may be more permeable to cells, less susceptible to degradation, and less apt to elicit an immune response than large molecules. Small molecules, such as peptide mimetics of antibodies and cytokines, as well as small molecule toxins are known in the art. See, e.g., Casset et al. (2003) *Biochem. Biophys. Res. Commun.* 307:198-205; Muyldermans (2001) *J. Biotechnol.* 74:277-302; Li (2000) *Nat. Biotechnol.* 18:1251-1256; Apostolopoulos et al. (2002) *Curr. Med. Chem.* 9:411-420; Monfardini et al. (2002) *Curr. Pharm. Des.* 8:2185-2199; Domingues et al. (1999) *Nat. Struct. Biol.* 6:652-656; Sato and Sone (2003) *Biochem. J.* 371:603-608; U.S. Pat. No. 6,326,482.

"Specifically" or "selectively" binds, when referring to a ligand/receptor, antibody/antigen, or other binding pair, indicates a binding reaction which is determinative of the presence of the protein in a heterogeneous population of proteins and other biologics. Thus, under designated conditions, a specified ligand binds to a particular receptor and does not bind in a significant amount to other proteins present in the sample. The antibody, or binding composition derived from the antigen-binding site of an antibody, of the contemplated method binds to its antigen, or a variant or mutein thereof, with an affinity that is at least two fold greater, preferably at least ten times greater, more preferably at least 20-times greater, and most preferably at least 100-times greater than the affinity with any other antibody, or binding composition derived thereof. In a preferred embodiment the antibody will have an affinity for the desired target that is greater than about $10^9$ liters/mol, as determined, e.g., by Scatchard analysis. Munsen et al. (1980) *Analyt. Biochem.* 107:220-239.

An antibody that "specifically binds" to IL-23 or IL-23 receptor does not bind to proteins that do not comprise the IL-23-derived sequences, i.e. "specificity" as used herein relates to IL-23 specificity, and not any other sequences that may be present in the protein in question. For example, as used herein, an antibody that "specifically binds" to IL-23 will typically bind to FLAG-hIL-23, which is a fusion protein comprising IL-23 and a FLAG® peptide tag, but it does not bind to the FLAG® peptide tag alone or when it is fused to a protein other than IL-23. Depending on the context, specificity for IL-23 may also refer to the ability to bind to IL-23 (or its receptor) but not to other proteins, such as IL-12 (or its receptor).

II. General

Although IL-23 and IL-12 are both heterodimeric cytokines sharing a common subunit and a common receptor subunit, recent results have suggested that their roles in inflammation and host defense are more antagonistic than overlapping. Interleukin-23 (IL-23) is a heterodimeric cytokine comprised of two subunits, i.e., p19 and p40. The p19 subunit is structurally related to IL-6, granulocyte-colony stimulating factor (G-CSF) and the p35 subunit of IL-12. The p40 subunit is part of the cytokine IL-12, which is composed of p35 and p40. Heterodimeric IL-12 is often referred to as IL-12p70. IL-23 mediates signaling by binding to a heterodimeric receptor, comprised of IL-23R and IL-12Rβ1. The IL-12Rβ1 subunit is shared by the IL-12 receptor, which is composed of IL-12Rβ1 and IL-12Rβ2. IL-23 and IL-23 receptor, and their respective IL-23-specific subunits, are disclosed at WO 99/05280, WO 01/18051, WO 00/73451, and WO 01/85790.

A number of early studies on IL-12 involved a genetic deficiency in p40 (p40 knockout mouse; p40KO mouse), but it was subsequently realized with the discovery of IL-23 that such mice were deficient in both IL-12 and IL-23. Oppmann et al. (2000) *Immunity* 13:715-725; Wiekowski et al. (2001) *J. Immunol.* 166:7563-7570; Parham et al. (2002) *J. Immunol.* 168:5699-708; Frucht (2002) *Sci STKE* 2002, E1-E3; Elkins et al. (2002) *Infection Immunity* 70:1936-1948. These results changed the interpretation of many of the early observations that were originally thought to relate to IL-12 and the Th1 response.

Recent studies have suggested a greater diversification of the CD4+ T-cell effector repertoire than that encompassed by the Th1/Th2 paradigm. Th17 cells are now thought to be a separate lineage of effector Th cells contributing to immune pathogenesis previously attributed to the Th1 lineage. Although the pathways leading to Th17 differentiation are still unclear (Dong (2006) *Nat Rev Immunol* 6:329), IL-23 is a critical cytokine for the generation and maintenance of this lineage (Trinchieri et al. (2003) *Immunity* 19:641). While both IL-12 and IL-23 can induce IFN-γ expression in CD4+ T-cells, IL-23 alone facilitates production of the proinflammatory cytokine IL-17 by Th cells.

Despite many similarities, there is increasing evidence that IL-12 and IL-23 drive divergent immunological pathways. Th cells primed for IL-17 (Th17 cells) are responsible for various organ-related autoimmune diseases (Harrington et al. (2006) *Curr. Opin. Immunol.* 18:349), including experimental autoimmune encephalomyelitis (EAE) (Langrish et al. (2005) *J. Exp. Med.* 201:233), arthritis (Murphy et al. (2003) *J. Exp. Med.* 198:1951), colitis (Yen et al. (2006)*J. Clin. Invest.* 116:1310) and autoimmune myocarditis (Sonderegger et al. (2006) *Eur. J. Immunol.* 36:2844). Moreover, although less clear, the production of high levels IL-23/IL-17, more than IL-12/IFN-γ, better correlates with disease severity and immunopathology in diverse infections. Hunter (2005) *Nat. Rev. Immunol.* 5:521; Rutitzky (2005) *J. Immunol.* 175:3920. Other studies have suggested that IL-12 and IL-23 have distinct roles in host defense against *Klebsiella pneumoniae* (Happel et al. (2005) *J. Exp. Med.* 202:761) and *Citrobacter rodentium* (Mangan et al. (2006) *Nature* 441:231). These studies suggest that IL-12 and IL-23 have distinct roles in promoting antimicrobial immune responses and diseases in vivo.

The different roles of IL-12 and IL-23 in inflammation and host defense have important implications for chronic infections, such as chronic fungal infection. Although inflammation is required for prompt control of fungal infections, resolution of inflammation is essential for maintaining the balance between protection and immunopathology in infections and associated diseases. Han and Ulevitch (2005) *Nat. Immunol.* 6:1198. Prolonged inflammation is a hallmark of a wide range of chronic diseases and autoimmunity. Han & Ulevitch (2005). For *Candida*, failure to resolve inflammation is associated with defective fungal clearance. This unresolved *Candida* infection results in chronic mucocutaneous candidiasis (CMC). CMC is associated with autoimmune polyendocrinopathy-candidiasis-ectodermal dystrophy, a condition of dysfunctional T cell activity. Ryan et al. (2005) *J. Allergy Clin. Immunol.* 116:1158. CMC also encompasses a variety of clinical disorders of unknown immunopathogenesis. Lilic (2002) *Curr. Opin. Infect. Dis.* 15:143. For *Aspergillus*, persistent inflammation with intractable infection is common in non-neutropenic patients after allogeneic hematopoietic stem cell transplantation (Ortega et al. (2006) *Bone Marrow Transplant* 37:499) as well as in allergic fungal diseases (Schubert (2006) *Clin. Rev. Allergy Immunol.* 30:205). For the last two decades the immunopathogenesis of fungal infections and associated inflammatory diseases has been explained primarily in terms of Th1/Th2 balance as affected by a combination of different types of regulatory T cells (T reg). Romani (2004) *Nat. Rev. Immunol.* 4:1; Romani and Puccetti (2006) *Trends Microbiol.* 14:183.

Although inflammation is an essential component of the protective response to fungi, its dysregulation may significantly worsen fungal diseases. As disclosed herein, IL-23 and IL-17 negatively regulate IL-12/Th1-mediated immune resistance to fungi and play an inflammatory role previously attributed to uncontrolled Th1 cell responses. IL-23 is known to promote the survival of Th17 cells (which produce IL-17 and cause inflammation) and antagonize the IL-12-mediated Th1 response (which involves production of interferon-γ (IFN-γ)). Langrish et al. (2004) *Immunol. Rev.* 202:96. As demonstrated herein, IL-23 counter-regulation of IL-12 production and Th1 responses results in uncontrolled inflammation and growth of *Candida albicans* and *Aspergillus fumigatus*, two major human fungal pathogens. Both IL-23 and IL-17 subvert the inflammatory program and anti-fungal activity of neutrophils, resulting in severe tissue inflammatory pathology associated with infection. In summary, IL-23-driven inflammation promotes infection and impairs antifungal immune resistance. See also Zelante et al. (2007) *Eur. J. Immunol.* 37:2695, and related commentary at Cooper (2007) *Eur. J. Immunol.* 37:2680. Modulation of the inflammatory response by antagonism of IL-23 represents a represents a promising strategy to stimulate protective immune responses to fungi.

The present invention provides compositions and methods for the treatment of infection, such as chronic infections, by blocking the activity of IL-23 and/or IL-17 to reduce the effects of Th17 cells and allow a robust Th1 response to emerge and eliminate the infected cells or organisms. In the optimal case the result is a sterile cure in which the infection is fully resolved (i.e. treatment may be discontinued without recurrence of the infection).

The same reasoning regarding the role of Th17 cells in maintaining a counter-productive inflammatory state applies in the case of chronic viral and bacterial infection, such as tuberculosis (TB). Cytokines are the soluble mediators of immune cells. The following cytokines have been detected in pleural or bronchoalveolar lavage (BAL) fluids of patients infected with TB: IL-1β, TNFα, IFNγ, TGFβ, and IL-12. See, e.g., Crystal, et al. (eds.) (1997) *The Lung: Scientific Foundations*, Lippincott-Raven, New York, N.Y., pp. 2381-2394. IFN-γ and TNFα have been shown to play important roles in the control of mycobacterial infections. See, e.g., Cooper et al. (1993) *J. Exp. Med.* 178:2243; Flynn et al. (1993) *J. Exp. Med.* 178:2249; Kindler et al. (1989) *Cell* 56:731; Cheuse et al. (1994) *Am. J. Pathol.* 145:1105. To the extent that IL-23 promotes the survival of Th17 cells, which reduces IL-12 driven IFN-γ production, antagonist of IL-23 activity may be expected to enhance resolution of bacterial infection.

The literature suggest that treatment with antagonists of IL-23 may be safer than treatment with antagonists of IL-12, e.g. in the treatment of autoimmune disorders or chronic infection. Chackerian et al. describe experiments in which elimination of IL-23 activity, either through antibody neutralization or genetic elimination in $p19^{-/-}$ knockout (KO) mice, did not compromise immunity to mycobacterial (BCG) infection. Chackerian et al. (2006) *J. Exp. Med.* 74:6092. The course of infection in IL-23p19 KO mice was indistinguishable from that in wildtype mice, and the numbers of bacterial colony forming units in anti-IL-23p19-treated mice did not differ from the number in isotype-control-treated mice. In contrast, IL-12 deficient KO mice failed to control the growth of BCG, and antibody blocking of IL-12 correlated with significantly higher numbers of CFU in the spleen, livers and lungs as compared to isotype-control-treated mice. These results suggest that IL-23 does not play a significant role in host defense against mycobacteria in the presence of IL-12, and therefore that selective inhibition of IL-23 may be safer than treatments that involve IL-12 neutralization (either with or without concurrent IL-23 neutralization). The results presented herein extend these results to suggest that antagonists of IL-23 are not only safer, in that they don't compromise host defense, but they may in fact be beneficial in helping to resolve chronic infections caused by dysregulation of IL-23/11:17 inflammation.

The experiments in Chackerian et al. (2006) were not designed to address the issue of whether blocking IL-23 would enhance clearance of pre-existing chronic mycobacterial infections. Control mice (WT mice, untreated or treated with isotype control antibody only) were able to effectively clear the infections, rather than developing a chronic infection. In both the KO mice and the antibody-blocking experiments in Chackerian et al. (2006), IL-23 activity was eliminated prior to infection with intravenous BCG, rather than after infection. The experiments described herein involved fungal, rather than mycobacterial, infections. In addition, the experiments described at Examples 4 and 5 herein include experiments using intragastric and intranasal administration of fungal pathogens, rather than intravenous administration. Direct delivery of these fungal pathogens to lung and stomach provides a more physiologically relevant disease model than intravenous delivery. The tissues infected with fungal pathogens in the experiments described herein have been suggested as the tissues in which the Th17 response may have its most important physiological role, i.e. the mucosal barrier of the lung and gut. Cua and Kastelein (2006) *Nature Immunol.* 7:557. In addition, anti-IL-23p19 and anti-IL-17 antibodies were administered five hours after infection in the experiments disclosed herein, rather than prior to infection.

III. Experimental Results in Fungal Infections

Prolonged inflammation is a hallmark of a wide range of chronic diseases and autoimmunity. Han & Ulevitch (2005). Before the discovery of IL-23 and its recently documented role in autoimmune inflammation (Cua et al. (2003) *Nature* 421:744; Langrish et al. (2005)*J. Exp. Med.* 201:233), IL-12, by initiating and maintaining Th1 responses, was thought to be responsible for overreacting immune and autoimmune disorders. This was also true of fungal infections and diseases where immunoregulation proved to be essential in fine-tuning inflammation and uncontrolled Th1/Th2 antifungal reactivity. Ryan et al. (2005); Romani (2004); Romani & Puccetti (2006).

The results of the present study show that the IL-23/IL-17 axis, and not an uncontrolled Th1 response, is associated with defective pathogen clearance, failure to resolve inflammation and to initiate protective immune responses to *Candida* and

*Aspergillus*. Thus, the new findings may serve to accommodate the paradoxical association of chronic inflammatory responses with intractable forms of fungal infections where fungal persistence occurs in the face of an ongoing inflammation.

Both IL-23 and IL-17 impaired the antifungal effector activities of PMN even in the presence of IFN-γ, a finding suggesting that the Th 17 effector pathway prevails over the Th1 pathway. In addition, both cytokines activated the inflammatory program of PMN by counteracting the IFN-γ-dependent activation of indoleamine 2,3-dioxygenase (IDO), known to limit the inflammatory status of PMN against fungi (Bozza et al. (2005) *J. Immunol.* 174:2910), as well as by inducing the release of MMP9 and MPO which likely accounts for the high inflammatory pathology and tissue destruction associated with Th17 cell activation.

The action on IDO is of interest. DO is expressed in *C. albicans* and is involved in tryptophan auxotrophy-dependent inhibition of fungal germination. Bozza et al. (2005). Similar to IDO blockade, and as opposed to IFN-γ (Kalo-Klein et al. (1990) *Infect. Immun.* 58:260), IL-17 promoted fungal germination (data not shown), a finding suggesting an action on fungal IDO, an enzyme that is highly responsive to signals from the mammalian host immune system. Mellor and Munn (2004) *Nat. Rev. Immunol.* 4:762. Therefore, the function of the Th17 pathway may go beyond its ability to promote inflammation and subvert antimicrobial immunity, as already described for other infections (McKenzie et al. (2006) *Trends Immunol.* 27:17), to include an action on fungal morphology and virulence. This may translate in concomitant IL-4+Th2 cell activation, known to be strictly dependent on high levels fungal growth (Mencacci et al. (1996) *Infect. Immun.* 64:4907) and further preventing Th1 functioning.

As already described for other infections (Cruz et al. (2006) *J. Immunol.* 177:1416; Park et al. (2005) *Nat. Immunol.* 6:1133), the Th1 or Th17 pathways were reciprocally regulated in both fungal infections. This finding suggests that the occurrence of either pathway in response to fungi is under strict environmental control. Regulation may occur at different stages. One obvious level of regulation is represented by IFN-γ which is known to regulate the induction of Th17 cells. Cruz et al. (2006); Park et al. (2005). The IL-23/IL-17 axis was indeed heightened in condition of IFN-γ deficiency in both infections, and the number of IFN-γ-producing cells increased upon IL-17 neutralization. These data are in line with the notion that IFN-γ is required for IL-12 responsiveness in mice with candidiasis. Cenci et al. (1998) *J. Immunol.* 161:3543.

More important, the production of IL-12 was higher in $p19^{-/-}$ DC and production of IL-23 higher in $p35^{-/-}$ DC, and both cytokines were cross-regulated in WT DC. These findings suggest that these cytokines are reciprocally regulated at the level of DC production. Becker et al. (2006) *J. Immunol.* 177:2760. However, because inflammatory DC more than tolerogenic DC appear to produce IL-23 in response to fungi, this implies that the Th1/Th17 balance also depends on the reciprocal regulation between DC subsets at different body sites.

The finding that IL-23 is produced in response to fungi in condition of high-threat inflammation, that is by inflammatory DC in response to high yeast number through the TLR-/MyD88 pathway, has important implications. Not only does it point to IL-23 as an important molecular link between the inflammatory processes and fungal virulence, but it also establishes a scenario whereby a vicious circle may be at work. Because $p19^{-/-}$ mice produce less IL-17 and TGF-β showed a non-essential role in Th17 activation and/or maintenance against fungi, it is conceivable that IL-23 acts as a proximal mediator of IL-17. In this scenario, the uncontrolled fungal growth may perpetuate the activation of pathogenic Th17 cells implicating concomitant activation of nonprotective Th2 cells.

One interesting observation in this study was that although microbial stimuli may be a major inducer of IL-23 secretion, adaptive immune processes may also modulate its production. In support of this we have provided evidence that IL-23 secretion by DC was dramatically increased in the presence of T cells, a finding suggesting that activated T cells may provide a positive feedback loop for further induction of IL-23.

The above considerations may help to accommodate fungi, either commensals or ubiquitous, within the immune homeostasis and its dysregulation. If the ability to subvert the inflammatory program through the activation of the IL-23/IL-17 axis may eventually lead to immune dysregulation, their ability to activate T reg cells, integral and essential components of protective immunity to either *Candida* or *Aspergillus* (Romani & Puccetti (2006)), may represent a mechanism whereby dysregulated immunity is prevented. In this regard, a functional antagonism between Th17 and T reg cells has been described (Bettelli & Kuchroo (2005) *J. Exp. Med.* 201:169), including the inhibitory role of IL-10 in the development of IL-17-producing cells in vivo. Kullberg et al. (2006) *J. Exp. Med.* 203:2485. It is possible therefore that a reciprocal pathway for the generation of Th17 and T reg cells may also take place in fungal infections. We have found no evidence of CD4+CD25+ T reg cell activation in $p35^{-/-}$ mice after infection, a finding suggesting that Th17 and T reg cells are mutually exclusive. CD4+CD25+ T reg cells were instead observed in $p19^{-/-}$ mice, despite a significant decrease of IL-10 production, which is consistent with the ability of IL-23 to up-regulate IL-10 production by T cells. Vanden Eijnden et al. (2005) *Eur. J. Immunol.* 35:469-475.

Another important observation of the present study is that the IL-23/IL-17-dependent pathway may provide some antifungal resistance in condition of IFN-γ deficiency, through a p35-dependent pathway. That IL-23 may serve a protective role in condition of IL-12 deficiency has already been reported in chronic cryptococcosis (Kleinschek et al. (2006) *J. Immunol.* 176:1098), mycobacterial infection (Khader et al. (2005) *J. Immunol.* 175:788) and acute pulmonary *Klebsiella pneumoniae* infection (Happel et al. (2005) *Infect. Immun.* 73:5782), where the protection correlated with an ability of IL-23 to activate antigen-specific IFN-γ-producing CD4+ T cells, independently of IL-12p70, and to recruit PMN mediating pathogen clearance. Happel et al. (2005) *J. Exp. Med.* 202:761. As a matter of fact, in experimental *Helicobacter hepaticas*-induced colitis, IL-23 has clearly been shown to drive both IFN-γ- and IL-17-producing cells. Kullberg et al. (2006). Our results seem to suggest a further level of cross-regulation between the Th1 and the Th17 pathways in infections that implicates a p35-dependent pathway in the action of IL-23. Ultimately, the ability of IL-23 to process initial inflammatory danger signals before the onset of the appropriate immune effector functions dominated by the IL-12-dependent axis (McKenzie et al. (2006)) is consistent with antagonist as well as collaborative activities between this pair of cytokines.

Collectively, the data presented in this study demonstrate a previously undefined role for the IL-23-dependent Th17 lineage in fungal infections that has important implications for mechanisms of host defense, immune homeostasis and immunity to fungi. Moreover, they show a molecular connection between the failure to resolve inflammation and lack of antifungal immune resistance. The current results suggest strategies for immune therapy of fungal infections that attempt to limit inflammation to stimulate an effective immune response.

IV. IL-23 Antagonists

Antagonists of IL-23 include any substance or method capable of inhibiting one or more biological activities of IL-23. Such activities include binding to the IL-23 (comprising p19 and p40 subunits), IL-23 receptor (comprising IL-23R and IL-12Rβ1 subunits) and promotion and maintenance of Th17 cells. Antagonists may comprise, e.g., small molecules, antibodies or antibody fragments, peptide mimetics, aptamers (e.g. as disclosed in U.S. Patent Application Publication No. 2006-0193821), soluble receptor derived from on the extracellular region of a subunit of the IL-23 receptor, and nucleic acid based antagonists.

Nucleic acid-based antagonists of IL-23 include antisense nucleic acids and siRNA directed to the IL-23p19 gene or the IL-23R gene. For general siRNA methodology, see WO 2006/06060598. See also Arenz and Schepers (2003) *Naturwissenschaften* 90:345; Sazani and Kole (2003) *J. Clin. Invest.* 112:481; Pirollo et al. (2003) *Pharmacol. Therapeutics* 99:55; Wang et al. (2003) *Antisense Nucl. Acid Drug Devel.* 13:169. Antisense and siRNA molecules can be designed based on the known sequences of human IL-23p19 and IL-23R mRNA. mRNA and amino acid sequences for human IL-23p19 are found at GenBank Accession Nos. NM_016584 and NP_057668, respectively. cDNA and amino acid sequences for human IL-23R are found at GenBank Accession Nos. AF461-422 and AAM44229, respectively. The invention also provides compositions for RNA interference.

Methods of producing and using siRNA are disclosed, e.g., at U.S. Pat. No. 6,506,559 (WO 99/32619); U.S. Pat. No. 6,673,611 (WO 99/054459); U.S. Pat. No. 7,078,196 (WO 01/75164); U.S. Pat. No. 7,071,311 and PCT publications WO 03/70914; WO 03/70918; WO 03/70966; WO 03/74654; WO 04/14312; WO 04/13280; WO 04/13355; WO 04/58940; WO 04/93788; WO 05/19453; WO 05/44981; WO 03/78097. U.S. patents are listed with related PCT publications. Exemplary methods of using siRNA in gene silencing and therapeutic treatment are disclosed at PCT publications WO 02/096927 (VEGF and VEGF receptor); WO 03/70742 (telomerase); WO 03/70886 (protein tyrosine phosphatase type IVA (Pr13)); WO 03/70888 (Chk1); WO 03/70895 and WO 05/03350 (Alzheimer's disease); WO 03/70983 (protein kinase C alpha); WO 03/72590 (Map kinases); WO 03/72705 (cyclin D); WO 05/45034 (Parkinson's disease). Exemplary experiments relating to therapeutic uses of siRNA have also been disclosed at Zender et al. (2003) *Proc. Nat'l. Acad. Sci. (USA)* 100:7797; Paddison et al. (2002) *Proc. Nat'l. Acad. Sci. (USA)* 99:1443; and Sah (2006) *Life Sci.* 79:1773. siRNA molecules are also being used in clinical trials, e.g., of chronic myeloid leukemia (CML) (ClinicalTrials.gov Identifier: NCT00257647) and age-related macular degeneration (AMD) (ClinicalTrials.gov Identifier: NCT00363714).

Although the term "siRNA" is used herein to refer to molecules used to induce gene silencing via the RNA interference pathway (Fire et al. (1998) *Nature* 391:806), such siRNA molecules need not be strictly polyribonucleotides, and may instead contain one or more modifications to the nucleic acid to improve its properties as a therapeutic agent. Such agents are occasionally referred to as "siNA" for short interfering nucleic acids. Although such changes may formally move the molecule outside the definition of a "ribo"nucleotide, such molecules are nonetheless referred to as "siRNA" molecules herein. Other variants of nucleic acids used to induce gene silencing via the RNA interference pathway include short hairpin RNAs ("shRNA"), for example as disclosed in U.S. Pat. Application Publication No. 20060115453. Nucleic acid-based inhibitors may be delivered, e.g., by transformation with a recombinant vector such as a plasmid or a virus (e.g. as naked DNA), or by gene therapy with any of known gene therapy vector (e.g. adeno-associated virus (AAV), adenovirus, a retrovirus or a lentivirus). Nucleic acids may be delivered by transformation, electroporation, biolistic bombardment or other methods known in the art.

Antibody antagonists of IL-23 for use in the compositions and methods of the present invention include antibodies to IL-23 and antibodies to IL-23 receptor. Exemplary antagonist antibodies to IL-23 include the anti-human IL-23p19 antibodies, and fragments thereof, as disclosed in commonly-assigned U.S. Provisional Patent Application Nos. 60/891,409 and 60/891,413 (both filed 23 Feb. 2007), in U.S. Patent Application Publication Nos. 2007-0009526 and 2007-0048315, and in International Patent Publication Nos. WO 2007/076524, WO 2007/024846 and WO 2007/147019. Antibody antagonists to IL-23 also include antibodies that bind to the IL-12p40 subunit when that subunit is bound to IL-23p19, but not when it is bound to IL-12p35. See, e.g., U.S. Patent Application Publication No. 2005-0137385 and U.S. Pat. No. 7,252,971. Exemplary antagonist antibodies to IL-23 include anti-human IL-23 receptor antibodies, e.g. anti-IL-23R antibodies, and fragments thereof. Exemplary antagonist antibodies to IL-23R are disclosed in commonly-assigned U.S. Provisional Patent Application No. 60/892,104 (filed 28 Feb. 2007) and 60/945,183 (filed 20 Jun. 2007). Antagonists of IL-23 also include bispecific antibodies.

Regions of increased antigenicity can be used for antibody generation. Regions of increased antigenicity of human p19 occur, e.g., at amino acids 16-28; 57-87; 110-114; 136-154; and 182-186 of GenBank AAQ89442 (gi: 37183284). Regions of increased antigenicity of human IL-23R occur, e.g., at amino acids 22-33; 57-63; 68-74; 101-112; 117-133; 164-177; 244-264; 294-302; 315-326; 347-354; 444-473; 510-530; and 554-558 of GenBank AAM44229 (gi: 21239252). Analysis was by a Parker plot using Vector NTI® Suite (Informax, Inc., Bethesda, Md.). The present invention also provides an IL-23 antagonist that is a soluble receptor, i.e., comprising an extracellular region of IL-23R, e.g., amino acids 1-353 of GenBank AAM44229, or a fragment thereof, where the extracellular region or fragment thereof specifically binds to IL-23. Mouse IL-23R is GenBank NP_653131 (gi: 21362353). Muteins and variants are contemplated, e.g., pegylation or mutagenesis to remove or replace deamidating Asn residues.

Additional potential methods of antagonizing the activity of IL-23 for use in the methods and compositions of the present invention include administering filamentous hemagglutinin (FHA) (WO 2006/109195) and vaccinating to generate an immune response against IL-23 (WO 2005/058349).

In one embodiment, an antagonist of an IL-17 producing (Th17) cell encompasses a reagent that specifically modulates the activity of a Th17 cell, e.g., without substantial influence on the activity of, e.g., a naïve T cell, Th1-type T cell, TH2-type T cell, epithelial cell, and/or endothelial cell. The reagent can modulate expression or activity of, e.g., a transcription factor (e.g. RORγt) or adhesion protein, of the IL-17 producing cell. In addition, an antagonist of IL-23, TGF-β, or IL-6 may decrease the creation and survival of Th17 cells, and an antagonist of IL-17 may decrease the inflammatory effects (e.g. neutrophil recruitment) of such cells.

Monoclonal, polyclonal, and humanized antibodies can be prepared (see, e.g., Sheperd and Dean (eds.) (2000) *Monoclonal Antibodies*, Oxford Univ. Press, New York, N.Y.; Kontermann and Dubel (eds.) (2001) *Antibody Engineering*, Springer-Verlag, New York; Harlow and Lane (1988) *Antibodies A Laboratory Manual*, Cold Spring Harbor Laboratory Press, Cold Spring Harbor, N.Y., pp. 139-243; Carpenter, et al. (2000) *J. Immunol.* 165:6205; He et al. (1998) *J. Immunol.* 160:1029; Tang et al. (1999) *J. Biol. Chem.* 274:27371; Baca et al. (1997) *J. Biol. Chem.* 272:10678; Chothia et al. (1989) *Nature* 342:877; Foote and Winter (1992) *J. Mol. Biol.* 224:487; U.S. Pat. No. 6,329,511). Fully human antibodies may also be prepared, in which the entirety of the antibody sequence is derived from human germline sequences. Such fully human antibodies may be prepared from transgenic animals engineered to express human immunoglobulin genes, or by methods such as phage display and the like. See, e.g., Lonberg (2005) *Nature Biotechnol.* 23:1117; Vaughan et al. (1998) *Nature Biotechnol.* 16:535. Antibody fragments include Fab, Fab', Fab'-SH, Fv, single-chain Fv (scFv), F(ab')$_2$, and a diabodies. Pluckthun (1994) THE PHARMACOLOGY OF MONOCLONAL ANTIBODIES, vol. 113, Rosenburg and Moore eds., Springer-Verlag, New York, pp. 269-315; Holliger and Hudson (2005) *Nature Biotechnol.* 23:1126-1136.

The antibodies of the present invention also include antibodies with modified (or blocked) Fc regions to provide altered effector functions. See, e.g., U.S. Pat. No. 5,624,821; WO 2003/086310; WO 2005/120571; WO 2006/0057702; Presta (2006) *Adv. Drug Delivery Rev.* 58:640-656. Such modification can be used to enhance or suppress various reactions of the immune system, with possible beneficial effects in diagnosis and therapy. Alterations of the Fc region include amino acid changes (substitutions, deletions and insertions), glycosylation or deglycosylation, and adding multiple Fc. Changes to the Fc can also alter the half-life of antibodies in therapeutic antibodies, and a longer half-life would result in less frequent dosing, with the concomitant increased convenience and decreased use of material. Altered effector functions may be achieved by introducing specific mutations in the Fc portion of IgG1, e.g. by altering Asn297, e.g. to Ala or Gln (N297A or N297Q). See Presta (2005) *J. Allergy Clin. Immunol.* 116:731 at 734-35. Effector functions may also be changed by selecting different constant domains. For example, if a particular intended use of an antibody (or fragment) of the present invention were to call for altered effector functions, a heavy chain constant domain other than IgG 1 may be used. Although IgG1 antibodies provide for long half-life and for effector functions, such as complement activation and antibody-dependent cellular cytotoxicity (ADCC), such activities may not be desirable for all uses of the antibody. In such instances an IgG4 constant domain, for example, may be used. Altered effector functions are of particular relevance in the case of antibodies to IL-23 receptor (e.g. to IL-23R), since in one embodiment (not the only embodiment) the goal is not to induce killing of cells expressing IL-23 receptor, but instead merely to block IL-23 signaling in such cells. In this embodiment, the goal is to shift Th cells from the Th17 lineage toward the Th1 lineage, in which case cell killing would be unproductive.

Purification of antigen is not necessary for the generation of antibodies. Immunization can be performed by DNA vector immunization, see, e.g., Wang et al. (1997) *Virology* 228: 278. Alternatively, animals can be immunized with cells bearing the antigen of interest. Splenocytes can then be isolated from the immunized animals, and the splenocytes can fused with a myeloma cell line to produce a hybridoma (Meyaard et al. (1997) *Immunity* 7:283; Wright et al. (2000) *Immunity* 13:233; Preston et al. (1997) *Eur. J. Immunol.* 27:1911). Resultant hybridomas can be screened for production of the desired antibody by functional assays or biological assays, that is, assays not dependent on possession of the purified antigen. Immunization with cells may prove superior for antibody generation than immunization with purified antigen (Kaithamana et al. (1999) *J. Immunol.* 163:5157).

Antibody to antigen and ligand to receptor binding properties can be measured, e.g., by surface plasmon resonance (Karlsson et al. (1991) *J. Immunol. Methods* 145:229; Neri et al. (1997) *Nat. Biotechnol.* 15:1271; Jonsson et al. (1991) *Biotechniques* 11:620) or by competition ELISA (Friguet et al. (1985) *J. Immunol. Methods* 77:305; Hubble (1997) *Immunol. Today* 18:305). Antibodies can be used for affinity purification to isolate the antibody's target antigen and associated bound proteins. See, e.g., Wilchek et al. (1984) *Meth. Enzymol.* 104:3.

Antibodies will usually bind with at least a $K_D$ of about $10^{-6}$ M, typically at least $10^{-7}$ M, more typically at least $10^{-8}$ M, preferably at least about $10^{-9}$ M, and more preferably at least $10^{-10}$ M, and most preferably at least $10^{-11}$ M. See, e.g., Presta et al. (2001) *Thromb. Haemost.* 85:379; Yang et al. (2001) *Crit. Rev. Oncol. Hematol.* 38:17; Carnahan et al. (2003) *Clin. Cancer Res.* (Suppl.) 9:3982s.

Soluble receptors comprising the extracellular domain of IL-23R are useful in the compositions and methods of the present invention. Soluble receptors can be prepared and used according to standard methods. See, e.g., Jones et al. (2002) *Biochim. Biophys. Acta* 1592:251; Prudhomme et al. (2001) *Expert Opinion Biol. Ther.* 1:359; Fernandez-Botran (1999) *Crit. Rev. Clin. Lab Sci.* 36:165-224.

In one embodiment the compositions and methods of the present invention require antagonism of IL-23 and not antagonism of IL-12. There are currently several potential therapeutic agents under development that target the IL-12p40 subunit of both IL-12 and IL-23 that would block the activity of both IL-23 and IL-12. Such agents would not be suitable for use in this embodiment of the compositions and methods of the present invention since they would inhibit the robust IL-12-mediated Th1 response that the invention is intended to promote. Although it is in principle possible to develop an agent that binds to IL-12p40 only in the context of IL-23 but not in the context of IL-12 (see U.S. Patent Application Publication No. 2005-0137385 and U.S. Pat. No. 7,252,971), it is likely that the majority of agents targeting IL-12p40 will inhibit IL-12 and thus not be suitable for the present invention. The same argument applies with the shared receptor subunit of IL-23 and IL-12, IL-12Rβ1. Although it is in principle possible to develop an agent that binds to IL-12β1 only in the context of IL-23 receptor but not in the context of IL-12 receptor, it is likely that the majority of agents targeting IL-12Rβ1 will inhibit IL-12 receptor and thus not be suitable for the present invention. In contrast, agents that bind to and antagonize subunits specific to IL-23 or its receptor, i.e. p19 and IL-23R, respectively, are likely to be specific inhibitors of IL-23 rather than IL-12, and thus more suitable for use in the compositions and methods of the present invention.

Whether a potential therapeutic agent specifically inhibits IL-23 rather than IL-12 may be determined by any method known in the art. For example a potential IL-23-specific antagonist may be tested for its ability to block the binding of IL-23 to its receptor, or IL-12 to its receptor. Such blocking assays may be performed in solution (e.g. by fluorescence-activated cell sorting) or on a solid support (e.g. by enzyme-linked immunosorbent assay—ELISA). IL-23 and IL-12 receptor blocking can also be measured in a bioassay, such as a Ba/F3 cell proliferation assay. See e.g. Ho et al. (1995) *Mol. Cell. Biol.* (1995) 15:5043. In such binding assays, the potency and specificity of a potential IL-23 antagonist may be expressed as an IC50, or the concentration of the potential antagonist necessary to achieve a 50% reduction in IL-23 binding (or biological activity dependent on binding) under a given set of assay conditions. A lower IC50 indicates a more effective antagonist. The IL-23 specificity of a potential antagonist may be expressed as the ratio of the IC50 for inhibition of binding of IL-12 to its receptor to the IC50 for inhibition of binding of IL-23 to its receptor ($IC50_{IL-12}$/$IC50_{IL-23}$). In various embodiments a potential IL-23 specific antagonist is considered to be IL-23 specific if this ratio ($IC50_{IL-12}$/$IC50_{IL-23}$) is 1.5, 2, 3, 4, 5, 7, 10, 15, 20, 50, 100 or more. In preferred embodiments the levels of IL-23 and IL-12 used in inhibition assays are adjusted to ensure that at least one, and preferably both of the IL-23 and IL-12 assays, are performed in the linear dose response concentration range.

IL-23 and IL-12 also have different biological functions that may be used to determine specificity of antagonism. In contrast to IL-12, IL-23 preferentially stimulates memory as opposed to naëve T cell populations in both human and mouse. IL-23 activates a number of intracellular cell-signaling molecules, e.g., Jak2, Tyk2, Stat1, Stat2, Stat3, and Stat4. IL-12 activates this same group of molecules, but Stat4 response to IL-23 is relatively weak, while Stat4 response to IL-12 is strong. Oppmann et al. (2000); Parham et al. (2002) *J. Immunol.* 168:5699.

A potential IL-23-specific antagonist may also be tested for its ability to inhibit the amplification and survival of Th1 and Th17 cells by IL-12 and IL-23. An IL-23-specific antagonist will preferentially inhibit the IL-23-mediated amplification and survival of Th17 cells, but not the IL-12-mediated amplification and survival of Th1 cells. Th17 cells characteristically secrete IL-17 whereas Th1 cells characteristically secrete IFN-γ. Data from an exemplary Th1/Th17 assay is found at FIG. 2 of Langrish et al. (2005) *J. Exp. Med.* 201:233, which demonstrates that IL-23 promotes amplification and survival of IL-17 producing $CD4^+$ T cells, whereas IL-12 promotes amplification and survival of IFN-γ-producing $CD4^+$ T cells. In one embodiment of the present invention, an agent is considered to be an "IL-23-specific" antagonist (relative to IL-12) when it is able to inhibit IL-23-mediated amplification and survival of Th17 cells, while not inhibiting IL-12-mediated amplification and survival of Th1 cells. Inhibition of Th17/Th1 cell proliferation can be expressed as an IC50, or the concentration of the agent necessary to achieve a 50% reduction in the activity of IL-23 in promoting the amplification and survival of a particular T cell subset producing IL-17 or IFN-γ under a given set of assay conditions. An exemplary assay is provided at Example 13. The potency of an IL-23 antagonist in a bioassay like the one described in Example 13 may be expressed as the $IC50_{IL-23}$, i.e. the concentration of antagonist needed to reduce the activity of IL-23 to 50% of its uninhibited value. An analogous $IC50_{IL-12}$ may be determined for IL-12 and its activity in promoting production of IFN-γ producing cells. The IL-23-specificity of the antagonist can then be expressed as the ratio $IC50_{IL-12}$/$IC50_{IL-23}$. In various embodiments, the $IC50_{IL-12}$/$IC50_{IL-23}$ ratio for a validated IL-23-specific antagonist is 1.5, 2, 3, 4, 5, 7, 10, 15, 20, 50, 100 or more.

Production of IL-17A and IFN-γ may be measured by intracellular cytokine flow cytometry by fluorescence activated cell sorting (FACS®) analysis) with fluorescent reagents that bind to the cytokines, essentially as described in Langrish et al. (2005). It is important to define the threshold level of IL-17A or IFN-γ in a live $CD4^+$ T cell for that cell to be considered "IL-17 producing" or "IFN-γ producing." In one embodiment the threshold level is defined as the level at which 5% of live $CD4^+$ T cells are "IL-17 producing" or "IFN-γ producing" in a control sample of untreated cells. Exemplary untreated cells include draining lymph node (DLN) cells isolated from SJL mice (The Jackson Laboratories, Bar Harbor, Me., USA) immunized with proteolipid protein (PLP) cultured in the presence of PLP.

V. Compositions and Methods

To prepare pharmaceutical or sterile compositions including an antagonist of IL-23, the antagonist is admixed with a pharmaceutically acceptable carrier or excipient, see, e.g., *Remington's Pharmaceutical Sciences* and *U.S. Pharmacopeia: National Formulary*, Mack Publishing Company, Easton, Pa. (1984). Formulations of therapeutic agents may be prepared by mixing with physiologically acceptable carriers, excipients, or stabilizers in the form of, e.g., lyophilized powders, slurries, aqueous solutions or suspensions (see, e.g., Hardman, et al. (2001) *Goodman and Gilman's The Pharmacological Basis of Therapeutics*, McGraw-Hill, New York, N.Y.; Gennaro (2000) *Remington: The Science and Practice of Pharmacy*, Lippincott, Williams, and Wilkins, New York, N.Y.; Avis, et al. (eds.) (1993) *Pharmaceutical Dosage Forms: Parenteral Medications*, Marcel Dekker, NY; Lieberman, et al. (eds.) (1990) *Pharmaceutical Dosage Forms: Tablets*, Marcel Dekker, NY; Lieberman, et al. (eds.) (1990) *Pharmaceutical Dosage Forms Disperse Systems*, Marcel Dekker, NY; Weiner and Kotkoskie (2000) *Excipient Toxicity and Safety*, Marcel Dekker, Inc., New York, N.Y.).

The route of administration is by, e.g., topical or cutaneous application, injection or infusion by intravenous, intraperitoneal, intracerebral, intramuscular, intraocular, intraarterial, intracerebrospinal, intralesional, or pulmonary routes, or by sustained release systems or an implant. Injection of gene transfer vectors into the central nervous system has been described. See, e.g., Cua et al. (2001) *J. Immunol.* 166:602; Sidman et al. (1983) *Biopolymers* 22:547; Langer et al. (1981) *J. Biomed. Mater. Res.* 15:167; Langer (1982) *Chem. Tech.* 12:98; Epstein et al. (1985) *Proc. Natl. Acad. Sci. USA* 82:3688; Hwang et al. (1980) *Proc. Natl. Acad. Sci. USA* 77:4030; U.S. Pat. Nos. 6,350,466 and 6,316,024.

Selecting an administration regimen for a therapeutic agent depends on several factors, including the serum or tissue turnover rate of the agent, the level of symptoms, the immunogenicity of the agent, and the accessibility of the target cells in the biological matrix. Preferably, an administration regimen maximizes the amount of therapeutic agent delivered to the patient consistent with an acceptable level of side effects. Accordingly, the amount of agent delivered depends in part on the particular entity and the severity of the condition being treated. Guidance in selecting appropriate doses of antibodies, cytokines, and small molecules are available. See, e.g., Wawrzynczak (1996) *Antibody Therapy*, Bios Scientific Pub. Ltd, Oxfordshire, UK; Kresina (ed.) (1991) *Monoclonal Antibodies, Cytokines and Arthritis*, Marcel Dekker, New York, N.Y.; Bach (ed.) (1993) *Monoclonal Antibodies and Peptide Therapy in Autoimmune Diseases*, Marcel Dekker, New York, N.Y.; Baert et al. (2003) *New Engl. J. Med.* 348:601; Milgrom et al. (1999) *New Engl. J. Med.* 341:1966; Slamon et al. (2001) *New Engl. J. Med.* 344:783; Beniaminovitz et al. (2000) *New Engl. J. Med.* 342:613; Ghosh et al. (2003) *New Engl. J. Med.* 348:24; Lipsky et al. (2000) *New Engl. J. Med.* 343:1594.

Antibodies, antibody fragments, and cytokines can be provided by continuous infusion, or by doses at intervals of, e.g., one day, one week, or 1-7 times per week. Doses may be provided intravenously, subcutaneously, topically, orally, nasally, rectally, intramuscularly, intracerebrally, intraspinally, or by inhalation. In various embodiments the mode of administration is selected based on the primary locus of infection, e.g. the lung or GI tract.

A preferred dose protocol is one involving the maximal dose or dose frequency that avoids significant undesirable side effects. A total weekly dose is generally at least about 0.05 µg/kg, 0.2 µg/kg, 0.5 µg/kg, 1 µg/kg, 10 µg/kg, 100 µg/kg, 0.2 mg/kg, 1.0 mg/kg, 2.0 mg/kg, 10 mg/kg, 25 mg/kg, or 50 mg/kg. See, e.g., Yang et al. (2003) *New Engl. J. Med.* 349:427; Herold et al. (2002) *New Engl. J. Med.* 346:1692; Liu et al. (1999) *J. Neurol. Neurosurg. Psych.* 67:451; Portielji et al. (2003) *Cancer Immunol. Immunother.* 52:133. The desired dose of a small molecule therapeutic, e.g., a peptide mimetic, natural product, or organic chemical, is about the same as for an antibody or polypeptide, on a moles/kg basis.

An effective amount for a particular patient may vary depending on factors such as the condition being treated, the overall health of the patient, the method route and dose of administration and the severity of side effects, see, e.g., Maynard et al. (1996) *A Handbook of SOPs for Good Clinical Practice*, Interpharm Press, Boca Raton, Fla.; Dent (2001) *Good Laboratory and Good Clinical Practice*, Urch Publ., London, UK.

Typical veterinary, experimental, or research subjects include monkeys, dogs, cats, rats, mice, rabbits, guinea pigs, horses, and humans.

Determination of the appropriate dose is made by the clinician, e.g., using parameters or factors known or suspected in the art to affect treatment or predicted to affect treatment. Generally, the dose begins with an amount somewhat less than the optimum dose and it is increased by small increments thereafter until the desired or optimum effect is achieved relative to any negative side effects. Important diagnostic measures include those of symptoms of, e.g., the infection or infection levels. Preferably, a biologic to be used is derived from the same species as the animal targeted for treatment, or is modified to mimic a protein derived from the same species (e.g. humanized antibodies), thereby minimizing a humoral response to the reagent.

Methods for co-administration or treatment with a second therapeutic agent, e.g., a cytokine, steroid, chemotherapeutic agent, antibiotic, or radiation, are well known in the art. See, e.g., Hardman et al. (eds.) (2001) *Goodman and Gilman's The Pharmacological Basis of Therapeutics*, 10$^{th}$ ed., McGraw-Hill, New York, N.Y.; Poole and Peterson (eds.) (2001) *Pharmacotherapeutics for Advanced Practice: A Practical Approach*, Lippincott, Williams & Wilkins, Phila., Pa.; Chabner and Longo (eds.) (2001) *Cancer Chemotherapy and Biotherapy*, Lippincott, Williams & Wilkins, Phila., Pa. An effective amount of therapeutic will decrease the symptoms typically by at least 10%; usually by at least 20%; preferably at least about 30%; more preferably at least 40%, and most preferably by at least 50%.

The invention further provides use of antagonists of IL-23 or IL-23R, or both, in the manufacture of a medicament for the treatment of an infectious disease, including but not limited to a condition selected from the group consisting of a fungal infection, a persistent fungal infection, candidiasis, CMC, aspergillosis, cryptococcosis, a viral infection, a persistent viral infection, HIV infection, HBV infection, HCV infection, a baceterial infection, mycobacterial infection, an *M. tuberculosis* infection, an *M. bovis* infection and an *M. leprae* infection. In some embodiments, the medicament may comprise one or more additional therapeutic agents. In other embodiments the medicament of the present invention may be used in conjunction with one or more other therapeutic agents.

VI. Anti-idiotypic Antibodies

The invention further provides anti-idiotypic antibodies directed to therapeutic anti-IL-23 or anti-IL-23R antibodies of the present invention. An anti-idiotypic antibody is an antibody that recognizes unique determinants generally associated with the antigen-binding region of another antibody. The anti-idiotypic antibody can be prepared by immunizing an animal of the same species and genetic type (e.g., mouse strain) as the source of the original anti-IL-23 antibody with the anti-IL-23 antibody or a CDR containing region thereof. The immunized animal then generates antibodies to the idiotypic determinants of the immunizing antibody to produce an anti-idiotypic antibody. The anti-idiotypic antibody may also be used as an immunogen to induce an immune response in yet another animal, producing a so-called "anti-anti-Id antibody."

Anti-idiotypic antibodies may be used, for example, to determine the level of a therapeutic anti-IL-23 (or anti-IL-23R) antibody in a subject, e.g. in a bodily fluid (e.g. blood) of a subject undergoing anti-IL-23 therapy. Determination of the level of anti-IL-23 (or anti-IL-23R) antibody in a subject may be useful in maintaining a desired level of anti-IL-23 antibody in a subject since dosing may be modified in response to such determinations. Dosing may be increased or decreased (in frequency and/or amount per administration) to obtain a circulating level of anti-IL-23 antibody within a desired range of values. The desirable range may be determined by medical practitioners by methods typical in the art, and may depend on the therapeutic index for the anti-IL-23 (or anti-IL-23R) antibody or fragment thereof.

An anti-idiotypic antibody may be supplied in a form suitable for easy detection, including antibodies with polypeptide tags (e.g. the FLAG® tag), or coupled to dyes, isotopes, enzymes, and metals. See, e.g., Le Doussal et al. (1991) *New Engl. J. Med.* 146:169; Gibellini et al. (1998) *J. Immunol.* 160:3891; Hsing and Bishop (1999) *New Engl. J. Med.* 162:2804; Everts et al. (2002) *New Engl. J. Med.* 168:883. Various assay formats exist, such as radioimmunoassays (RIA), ELISA, and lab on a chip. U.S. Pat. Nos. 6,176,962 and 6,517,234.

VII. Kits

This invention further provides antagonists of IL-23 in kits for use in treatment of subjects (human or non-human) suffering from infections, such as chronic bacterial, mycobacterial, viral and fungal infections. In one embodiment, the kit comprises a compartment for containing an antagonist of IL-23, the antagonist of IL-23 itself (such as an antibody), and optionally instructions for use, one or more additional therapeutic agent or agents, and one or more medical devices for administration (e.g. a syringe or a disposable injector such as the Redipen™ injector device). The antagonist of IL-23 may be any of the agents described herein, including but not limited to, anti-p19 antibodies or p19-binding fragments thereof, anti-IL-23R antibodies or IL-23R-binding fragments thereof, or soluble IL-23R fragments.

The one or more additional therapeutic agents include, but are not limited to, non-steroidal anti-inflammatories (NSAIDS), steroids, IL-12 or an agonist thereof, and antagonists of cytokines such as IL-17A, IL-17F, TGF-β, IL-6, or their respective receptors. Antagonists for cytokines include antibodies that bind to the cytokine, its subunits, or its receptor. Although not all antibodies that bind to cytokines or their receptors are necessarily antagonists, such antagonist activity can readily be assessed by techniques commonly known in the art, such as a bioassay or receptor binding assay. Nucleic acid and amino acid sequences for various (human) cytokines and receptors are known, including IL-17A (NM_002190, NP_002181), IL-17F (NM_052872, NP_443104);

IL-17RA (NM_014339, NP 055154); IL-17RC (transcript variants NM 153461, NM 153460, NM_032732, and their respective translations).

The invention further provides kits comprising anti-idiotypic antibodies directed to therapeutic anti-IL-23 (or anti-IL-23R) antibodies of the present invention. In one embodiment, the kit comprises a compartment for containing the anti-idiotypic antibody, the anti-idiotypic antibody itself, and optionally instructions for use, one or more detection reagents, one or more devices for detection of the anti-idiotypic antibody (such as a microtiter plate), and one or more samples of the anti-IL-23 antibodies to be detected (or other positive control).

VIII. Uses

A prolonged asymptomatic preclinical period often occurs prior to the development of tuberculosis. Thus, IL-23 and IL-23R antagonist therapy can be commenced upon analysis of various diagnostic markers of TB. Patients exhibiting a positive tuberculin test or Mantoux test (see, e.g., Dale and Federman (2002)), as compared to normal non-infected patients, can be given IL-23 or IL-23R antagonist therapy to prevent the further growth of mycobacteria, or to clear an existing non-pathological infection. Patients with high levels of mycobacterium in biological samples, e.g., BAL, may also benefit from IL-23 and IL-23R antagonist therapy to prevent the further growth of mycobacteria and clear bacterial burdens in the lungs. Similar treatment may be used for patients having high mycobacterial DNA or RNA levels in clinical samples or a positive niacin test in culture. Also envisioned is the use of IL-23 and IL-23R antagonists in conjunction with pathologically symptomatic TB infections to lessen or clear bacterial burdens.

Bacterial infections that may be treated using the methods and compositions of the present invention include, but are not limited to, those caused by: *Staphylococcus aureus, Staphylococcus epidermidis; Streptococcus pneumoniae; Streptococcus agalactiae; Streptococcus pyogenes; Enterococcus* spp.; *Bacillus anthracis; Bacillus cereus; Bifidobacterium bifidum; Lactobacillus* spp.; *Listeria monocytogenes; Nocardia* spp.; *Rhodococcus equi* (*coccobacillus*); *Erysipelothrix rhusiopathiae Corynebacterium diptheriae; Propionibacterium acnes; Actinomyces* spp.; *Clostridium botulinum; Clostridium difficile; Clostridium perfringens; Clostridium tetani; Mobiluncus* spp., *Peptostreptococcus* spp.; *Neisseria gonorrhoeae; Neisseria meningitides; Moraxella catarrhalis; Veillonella* spp.; *Actinobacillus actinomycetemcomitans; Acinetobacter baumannii; Bordetella pertussis; Brucella* spp.; *Campylobacter* spp.; *Capnocytophaga* spp.; *Cardiobacterium hominis; Eikenella corrodens; Francisella tularensis; Haemophilus ducreyi; Haemophilus influenzae; Helicobacter pylori; Kingella kingae; Legionella pneumophila; Pasteurella multocida; Klebsiella granulomatis; Citrobacter* spp., *Enterobacter* spp.; *Escherichia coli; Klebsiella pneumoniae; Proteus* spp.; *Salmonella enteriditis; Salmonella typhi; Shigella* spp.; *Serratia marcescens; Yersinia enterocolitica; Yersinia pestis; Aeromonas* spp.; *Plesiomonas shigelloides; Vibrio cholerae; Vibrio parahaemolyticus; Vibrio vulnificus; Acinetobacter* spp.; *Flavobacterium* spp.; *Pseudomonas aeruginosa; Burkholderia cepacia; Burkholderia pseudomallei; Xanthomonas maltophilia* or *Stenotrophomonas maltophila; Bacteroides fragilis; Bacteroides* spp.; *Prevotella* spp.; *Fusobacterium* spp.; *Spirillum minus; Borrelia burgdorferi; Borrelia recurrentis; Bartonella henselae; Chlamydia trachomatis; Chlamydophila pneumoniae; Chlamydophila psittaci; Coxiella burnetii; Ehrlichia chaffeensis; Anaplasma phagocytophilum; Legionella* spp.; *Leptospira* spp.; *Rickettsia rickettsii; Orientia tsutsugamushi; Treponema pallidum.*

Mycobacterial infections that may be treated using the methods and compositions of the present invention include, but are not limited to, those caused by: *M. abscessus, M. africanum, M. asiaticum, Mycobacterium avium* complex (MAC), *M. avium paratuberculosis, M. bovis, M. chelonae, M. fortuitum, M. gordonae, M. haemophilum, M. intracellulare, M. kansasii, M. lentiflavum, M. leprae, M. liflandii, M. malmoense, M. marinum, M. microti, M. phlei, M. pseudoshottsii, M. scrofulaceum, M. shottsii, M. smegmatis, M. triplex, M. tuberculosis, M. ulcerans, M. uvium,* and *M. xenopi.*

The methods and compositions of the present invention may also be used to treat fungal conditions, including but not limited to, histoplasmosis, coccidioidomycosis, blastomycosis, aspergillosis, penicilliosis, candidiasis and cryptococcosis. Risk factors for mycoses include blood and marrow transplant, solid-organ transplant, major surgery (especially gastrointestinal surgery), AIDS, neoplastic disease, advanced age, immunosuppressive therapy, and prematurity in infants.

Fungal pathogens causing infections (and clinical syndromes) that may be treated using the methods and compositions of the present invention include, but are not limited to, *Candida albicans* (thrush, vaginal candidiasis, esophageal candidiasis), *Cryptococcus neoformans* (meningitis), *Histoplasma capsulatum* (disseminated infection with fever and weight loss), *Coccidioides immitis* (diffuse and focal pulmonary disease), *Blastomyces dermatitidis* (localized pulmonary disease and disseminated infection, including meningitis), *Aspergillus fumigatus* (pulmonary disease with fever, cough, and hemoptysis), and *Penicillium marneffei* (fever alone or with pulmonary infiltrates, lymphadenopathy, or cutaneous lesions). The methods and compositions of the present invention may also be used to treat infections with *Candida* species *C. glabrata, C. parapsilosis, C. tropicalis, C. krusei, C. lusitaniae, C. guilliermondii,* and *C. rugosa.* The preceding fungal pathogens (and clinical syndromes) are commonly associated with HIV infection.

The methods and compositions of the present invention may also be used to treat infections with *Candida* species such as *C. glabrata, C. parapsilosis, C. tropicalis, C. krusei, C. lusitaniae, C. guilliermondii,* and *C. rugosa.* The methods and compositions of the present invention may also be used to treat infections with *Aspergillus* species such as *A. flavus, A. niger, A. ustus* and *A. terreus.* Additional fungal pathogens include *Fusarium* species (e.g. *F. moniliforme, F. solani, F. oxysporum*) and *Scedosporium* species (e.g. *S. apiosperum, S. prolificans*). Additional fungal diseases include zygomycoses caused by species of *Rhizopus* (e.g. *R. oryzae, R. arrhizus*), *Rhizomucor, Absidia, Cunninghamella.*

Antagonists of IL-23 and IL-23R may be used alone or in conjunction with agents intended to enhance a Th1 response (e.g. IL-12 or agonists thereof) or inhibit a Th17 response (e.g. TGF-β antagonists; IL-6 antagonists; IL-17A and/or IL-17F antagonists), or both. Agonists and antagonists of the receptors for these cytokines may also be used. Such agents may include antibodies and antigen-binding fragments thereof, small molecules, siRNA and antisense nucleic acids. Antagonists of IL-23 and IL-23R may also be used in conjunction with anti-inflammatory agents, such as corticosteroids, e.g. prednisone.

The IL-17 antagonist may inhibit the expression of IL-17A, IL-17F, IL-17RA or IL-17RC or may inhibit IL-17 signaling by directly or indirectly interacting with one or more of these polypeptides to prevent a functional ligand-receptor interaction. In some preferred embodiments, the IL-17 antagonist is an antibody or antibody fragment that binds to and inhibits the activity of either IL-17A, IL-17F, IL-17RA or IL-17RC. In one particularly preferred embodiment, the IL-17 antagonist is a monoclonal antibody that specifically binds to IL-17A. Exemplary antagonist antibodies to IL-17A include the anti-human IL-17A antibodies, and fragments thereof, disclosed in commonly-assigned U.S. patent application Ser. No. 11/836,318 (filed 9 Aug. 2007), and in WO 2006/013107 and WO 2006/054059. In another embodiment the IL-17 antagonist comprises a bispecific antibody.

In one embodiment the IL-23 antagonist comprises a bispecific antibody that binds to and inhibits the activity of IL-23. Such bispecific antibodies may bind to IL-23p19 or IL-23R, and may also bind to the IL-17A, IL-17F, IL-17RA, IL-17RC. In other embodiments the IL-23 antagonist is a bispecific antibody that binds to IL-23p19 and IL-17 and inhibits the activity of IL-23 and IL-17. See, e.g., WO 2007/147019. Alternatively, IL-23 and IL-17 antagonist bispecific antibodies may bind to either IL-23 receptor (e.g. IL-23R) or IL-17 receptor (IL-17RA or IL-17RC), respectively, provided that they are antagonist antibodies. Bispecific antibodies that antagonize both IL-17 and IL-23 activity can be produced by any technique known in the art. For example, bispecific antibodies can be produced recombinantly using the co-expression of two immunoglobulin heavy chain/light chain pairs. See, e.g., Milstein et al. (1983) *Nature* 305:537-39. Alternatively, bispecific antibodies can be prepared using chemical linkage. See, e.g., Brennan et al. (1985) *Science* 229:81. Bifunctional antibodies can also be prepared by disulfide exchange, production of hybrid-hybridomas (quadromas), by transcription and translation to produce a single polypeptide chain embodying a bispecific antibody, or transcription and translation to produce more than one polypeptide chain that can associate covalently to produce a bispecific antibody. The contemplated bispecific antibody can also be made entirely by chemical synthesis. The bispecific antibody may comprise two different variable regions, two different constant regions, a variable region and a constant region, or other variations.

Antagonists of IL-23 and IL-23R may be used alone or co-administered with known antibacterials, such as isoniazid, rifampin, pyrazinamide, ethambutol, streptomycin, ciprofloxacin, and ofloxacin. Additional antibacterial agents include, but are not limited to, alatrofloxacin, azithromycin, baclofen, benzathine penicillin, cinoxacin, clarithromycin, clofazimine, cloxacillin, demeclocycline, dirithromycin, doxycycline, erythromycin, ethionamide, furazolidone, grepafloxacin, imipenem, levofloxacin, lorefloxacin, moxifloxacin HCl, nalidixic acid, nitrofurantoin, norfloxacin, ofloxacin, rifabutin, rifapentine, sparfloxacin, spiramycin, sulphabenzamide, sulphadoxine, sulphamerazine, ulphacetamide, sulphadiazine, sulphafurazole, sulphamethoxazole, sulphapyridine, tetracycline, trimethoprim, trovafloxacin, and vancomycin.

The methods and compositions of the present invention may be used to treat persistent viral infections, including but not limited to infections caused by HBV, HCV, HIV, human papillomavirus (HPV). Such chronic infections represent a failure of the immune response to eradicate the infection. Antagonists of IL-23 and IL-23R may be used alone or in conjunction with other antiviral agents, including but not limited to, abacavir, acyclovir, amantadine, amprenavir, delavirdine, didanosine, efavirenz, famciclovir, indinavir, an interferon alfa, ribavirin, lamivudine, nelfinavir, nevirapine, oseltamivir, penciclovir, ribavirin, ritonavir, saquinavir, stavudine, valacyclovir, zalcitabine, zanamivir, zidovudine (azidodeoxythymidine, AZT). Preferred interferon alfa agents include pegylated interferon alfa 2a and pegylated interferon 2b. Exemplary forms of interferon alpha are discussed in U.S. Pat. No. 6,923,966. The IL-23 antagonist may also be used in combination with viral specific agents, such as HCV protease or HCV polymerase inhibitors for chronic HCV infection, and CCR5 antagonists for chronic HIV infection.

Antagonists of IL-23 and IL-23R may also be used in conjunction with a therapeutic vaccine, e.g. gp120-depleted whole killed virus for HIV infection, a recombinant E1 protein for HCV infection, and viral E6 and E7 oncoproteins for HPV infection. See Berzofsky et al. (2004). Such therapeutic vaccines include DNA vaccines or viral vectors, optionally administered in a heterologous priming and boosting regimen in which a DNA vaccine is followed by a viral vector vaccine. Berzofsky et al. (2004).

Antagonists of IL-23 and IL-23R may be used alone or in conjunction with other antifungal agents, including but not limited to, posaconazole, fluconazole (U.S. Pat. No. 4,404,216), voriconazole, itraconazole (U.S. Pat. No. 4,267,179), ketoconazole (U.S. Pat. Nos. 4,144,346 and 4,223,036), liarozole, irtemazol, clotrimazole, miconazole, econazole, butoconazole, oxiconazole, sulconazole, tioconazole, and terconazole, substituted thiazoles, thiadiazole, oxadiazole, caspofungin, amphotericin B, nystatin, pimaricin, flucytosine (5-fluorocytosine), naftifine, terbinafine, butenafine, thiocarbonate tolnaftate, griseofulvin, amiodarone, ciclopirox, sulbentine, amorolfine, clioquinol, gentian violet, potassium iodide, sodium thiosulfate, carbol-fuchsin solution, and the echinocandins (e.g. caspofungin acetate, micafungin and anidulafungin).

The IL-23 and IL-23R antagonists of the present invention may be used in combination with standard antifungal agents at their usual dosages when used as single agents, or at lower dosages if there is any synergistic enhancement in efficacy when the drugs are used together. Fluconazole may be administered, e.g., at 400-800 mg/day. Voriconazole may be administered at 4 mg/kg bid. Itraconazole may be administered at 200-600 mg/day. Amphotericin B desoxycholate (D-AmB) may be administered at 0.5-1 mg/kg/day. General guidance as to the types of agents and treatment regimens that may be combined with the compositions and methods of the present invention may be found in practice guidelines published by the Infectious Diseases Society of America (IDSA) at Pappas et al. (2004) *Clin. Infect. Dis.* 38:161 (candidiasis) and Stevens et al. (2000) *Clin. Infect. Dis.* 30:696 (aspergillosis). Practice guidelines for the treatment of tuberculosis are found at International Standards for Tuberculosis Care, published Mar. 22, 2006 and endorsed by the IDSA.

In some embodiments of the present invention the subject having an infection, or suspected to have an infection, has been previously treated for the infection using other methods or compositions (i.e. not methods or compositions of the present invention). The previous treatment may include treatment with any of the antimicrobial agents, antibiotics, antifungal agents, antiviral agents disclosed herein, or any other treatment method or composition.

In some embodiments the subject will have a formal diagnosis of infection, optionally with an identification of the etiological agent, but in other embodiments the subject may not have a formal diagnosis, or may have a partial diagnosis limiting but not fully identifying the etiological agent. In other embodiments the subject is only suspected of having an infection. In other embodiments the subject is at risk of having or acquiring an infection, e.g. the subject is undergoing immunosuppressive therapy, is at risk of acquiring a fungal infection because of AIDS, etc. In some embodiments the subject having an infection, or suspected to have an infection, or at risk of having or acquiring an infection, is immunocompromised, e.g. due to AIDS, chemotherapy, transplant, old age.

Many modifications and variations of this invention can be made without departing from its spirit and scope, as will be apparent to those skilled in the art. The specific embodiments described herein are offered by way of example only, and the invention is to be limited by the terms of the appended claims, along with the full scope of equivalents to which such claims are entitled; and the invention is not to be limited by the specific embodiments that have been presented herein by way of example.

EXAMPLE 1

General Methods

Standard methods in molecular biology are described (Maniatis et al. (1982) *Molecular Cloning, A Laboratory Manual*, Cold Spring Harbor Laboratory Press, Cold Spring Harbor, N.Y.; Sambrook and Russell (2001) *Molecular Cloning, 3rd ed.*, Cold Spring Harbor Laboratory Press, Cold Spring Harbor, N.Y.; Wu (1993) *Recombinant DNA*, Vol. 217, Academic Press, San Diego, Calif.). Standard methods also appear in Ausbel et al. (2001) *Current Protocols in Molecular Biology*, Vols. 1-4, John Wiley and Sons, Inc. New York, N.Y., which describes cloning in bacterial cells and DNA mutagenesis (Vol. 1), cloning in mammalian cells and yeast (Vol. 2), glycoconjugates and protein expression (Vol. 3), and bioinformatics (Vol. 4).

Methods for protein purification including immunoprecipitation, chromatography, electrophoresis, centrifugation, and crystallization are described. Coligan et al. (2000) *Current Protocols in Protein Science*, Vol. 1, John Wiley and Sons, Inc., New York. Chemical analysis, chemical modification, post-translational modification, production of fusion proteins, glycosylation of proteins are described. See, e.g., Coligan, et al. (2000) *Current Protocols in Protein Science*, Vol. 2, John Wiley and Sons, Inc., New York; Ausubel, et al. (2001) *Current Protocols in Molecular Biology*, Vol. 3, John Wiley and Sons, Inc., NY, N.Y., pp. 16.0.5-16.22.17; Sigma-Aldrich, Co. (2001) *Products for Life Science Research, St. Louis, Mo.; pp.* 45-89; Amersham Pharmacia Biotech (2001) *BioDirectory*, Piscataway, N.J., pp. 384-391). Production, purification, and fragmentation of polyclonal and monoclonal antibodies is described. Coligan et al. (2001) *Current Protocols in Immunology*, Vol. 1, John Wiley and Sons, Inc., New York; Harlow and Lane (1999) *Using Antibodies*, Cold Spring Harbor Laboratory Press, Cold Spring Harbor, N.Y.; Harlow and Lane (1998). Standard techniques for characterizing ligand/receptor interactions are available. See, e.g., Coligan et al. (2001) *Current Protocols in Immunology*, Vol. 4, John Wiley, Inc., New York.

Methods for flow cytometry, including fluorescence activated cell sorting (FACS), are available (see, e.g., Owens et al. (1994) *Flow Cytometry Principles for Clinical Laboratory Practice*, John Wiley and Sons, Hoboken, N.J.; Givan (2001) *Flow Cytometry, 2nd ed.*; Wiley-Liss, Hoboken, N.J.; Shapiro (2003) *Practical Flow Cytometry*, John Wiley and Sons, Hoboken, N.J.). Fluorescent reagents suitable for modifying nucleic acids, including nucleic acid primers and probes, polypeptides, and antibodies, for use, e.g., as diagnostic reagents, are available (Molecular Probes (2003) *Catalogue*, Molecular Probes, Inc., Eugene, Oreg.; Sigma-Aldrich (2003) *Catalogue*, St. Louis, Mo.).

Standard methods of histology of the immune system are described. See, e.g., Muller-Harmelink (ed.) (1986) *Human Thymus: Histopathology and Pathology*, Springer Verlag, New York, N.Y.; Hiatt et al. (2000) *Color Atlas of Histology*, Lippincott, Williams, and Wilkins, Phila, Pa.; Louis, et al. (2002) *Basic Histology: Text and Atlas*, McGraw-Hill, New York, N.Y.

Software packages and databases for determining, e.g., antigenic fragments, leader sequences, protein folding, functional domains, glycosylation sites, and sequence alignments, are available. See, e.g., GenBank, Vector NTI® Suite (Informax, Inc, Bethesda, Md.); GCG Wisconsin Package (Accelrys, Inc., San Diego, Calif.); DeCypher® (TimeLogic Corp., Crystal Bay, Nev.); Menne, et al. (2000) *Bioinformatics* 16: 741-742; Menne et al. (2000) *Bioinformatics Applications Note* 16:741; Wren et al. (2002) *Comput. Methods Programs Biomed.* 68:177; von Heijne (1983) *Eur. J. Biochem.* 133:17; von Heijne (1986) *Nucleic Acids Res.* 14:4683.

EXAMPLE 2

Fungal Infection Model

Mouse strains for the study of fungal infections were obtained as follows. Female C57BL/6 and BALB/c mice, 8-10 wk old, were purchased from Charles River (Calco, Italy). Homozygous IL-12p35-, IL-23p19- or IL-12p40-deficient mice (hereafter referred to as $p35^{-/-}$, $p19^{-/-}$ and $p40^{-/-}$, respectively), TLR-2-, TLR-4-, MyD88- or TRIF-deficient mice (hereafter referred to as $TLR-2^{-/-}$, $TLR-4^{-/-}$, $MyD88^{-/-}$ or $TRIF^{-/-}$) mice on C57BL/6 background were bred under specific pathogen-free conditions at the Animal Facility of Perugia University, Perugia, Italy. Breeding pairs of $IFN-\gamma^{-/-}/p35^{-/-}$ mice, on BALB/c background, were provided by Dr. M. Colombo (Istituto Tumori, Milan, Italy). $IFN-\gamma^{-/-}$ and $IL-4^{-/-}$ mice, on BALB/c background, were also bred at the Animal Facility of Perugia University. Experiments were performed according to the Italian Approved Animal Welfare Assurance A-3143-01.

Fungal infections and their treatments were studied as follows. The origin and characteristics of the *C. albicans* strain used in this study have already been described. Bacci et al. (2002) *J. Immunol.* 168:2904. For gastrointestinal infection, $10^8$ *Candida* cells were injected intragastrically and quantification of fungal growth was expressed as CFU per organ (mean±SE) as described. Bacci et al. (2002). For the intravenous infection, mice received different amounts of the fungus in 0.5 ml, intravenously. The strain of *A. fumigatus* and the culture conditions were as described. Montagnoli et al. (2006) *J. Immunol.* 176:1712. Mice received two doses of $2 \times 10^7$ *Aspergillus* resting conidia intranasally. Fungi were suspended in endotoxin-free solutions (Detoxi-gel, Pierce, Rockford, Ill.) at <1.0 EU/ml, as determined by the *Limulus* amebocyte lysate (LAL) method. Fungal growth was quantified by the chitin assay, with results expressed as micrograms of glucosamine/organ. For histology, tissues were excised and immediately fixed in formalin, and sections (3-4 μm) of paraffin-embedded tissues were stained with periodic acid-Schiff reagent and examined. Bacci et al. (2002); Montagnoli et al. (2006). Infected animals were treated with 200 μg of p19-neutralizing Ab (Belladonna et al. (2006) *Cytokine* 34:161) or IL-17A-neutralizing mAb (TC11-18H10, PharMingen, San Diego, Calif.) administered i.p. five hours after infection. A total of 1 mg of purified anti-TGF-β1, -β2, -β3 mAb. (2G7) (Lucas et al. (1990) *J. Immunol.* 145:1415) was administered i.p. 5 and 24 h after the infection. Control mice were injected with PBS because no differences were observed between PBS-treated and isotype control-treated (each treatment) animals (n>6 for each group).

Cells were purified as follows. Gr-1+CD11b+ polymorphonuclear neutrophils (PMN, >98% pure on FACS analysis) were isolated from the peritoneal cavity of mice by magnetic-activating sorting using Ly-6G MicroBeads and MidiMacs (Miltenyi Biotech, Bergisch Gladbach, Germany). CD4+ T cells were purified from the mesenteric lymph nodes (MLN), thoracic lymph nodes (TLN) and spleens by magnetic-activated sorting using CD4 MicroBeads and MidiMacs (Miltenyi Biotech). DC were obtained from bone marrow cells cultured in Iscove's modified medium in the presence of 150 U/ml mouse rGM-CSF (Sigma-Aldrich, St. Louis, Mo.) and 75 U/ml rIL-4 (R&D Systems, Minneapolis, Minn.) for 7 days to obtain CD11b+ DC or 200 ng/ml FLT3-L (R&D Systems) for 9 days to obtain FL-DC. Romani et al. (2006) *Blood* 108:2265. Splenic DC (>99% CD11c+ and <0.1% CD3+) consisting of 90-95% CD8−, 5-10% CD8+, and 1-5% B220+ cells) were purified by magnetic activated sorting using CD11c MicroBeads and MidiMacs (Miltenyi Biotech). Zymosan from *Saccharomyces cerevisiae* (10 µg/ml, Sigma-Aldrich), ultra-pure LPS from *Salmonella minnesota* Re 595 (10 µg/ml, Labogen, Rho, Milan, Italy) and CpG oligonucleotides 2006 (CpGODN, 0.06 µM) were used as described. Bellocchio et al. (2004) *J. Immunol.* 173:7406.

DC cells were pulsed and cultured as follows. DC were exposed to live unopsonized fungi, with and without 10 ng/ml cytokines (from R&D Systems; Space Import-Export srl, Milan, Italy; and BD Biosciences—PharMingen, San Diego, Calif.) or neutralizing antibodies (10 µg/ml), at a 1:1 cell: fungus ratio, as described. Bacci et al. (2002); Montagnoli et al. (2006). Cells were harvested for RT-PCR at 12 h of culture, and supernatants were assessed for cytokine contents by ELISA. Splenic CD4+ T cells ($10^6$/ml) were cultured in flat-bottomed 96-well plates in the presence of $5 \times 10^5$ Candida-pulsed splenic DC for 5 days, with and without neutralizing antibodies (10 µg/ml), before cytokines quantification in culture supernatants. Unfractionated MLN or TLN cells were cultured with inactivated fungi as described (Montagnoli et al. (2006); Montagnoli et al. (2002) *J. Immunol.* 169:6298) before cytokine determination in culture supernatants 5 days later.

EXAMPLE 3

Antifungal Activity Assays

Assays of PMN phagocytosis of unopsonized *Candida* yeasts or *Aspergillus* conidia, and fungicidal activity, were conducted as described. Bellocchio et al. (2004). Results are expressed as the percentage of CFU inhibition (mean±SE). PMN were exposed to varying concentrations of IL-17 or IL-23 or to 50 ng/ml IFN-γ±IL-23/IL-17 (100 ng/ml) for 12 h before western blotting for IDO or for 60 min before the addition of fungi for an additional 60 min for studies of fungicidal activity and MMP9/MPO (mouse myeloperoxidase) determination. Gelatin zymography was performed as described. Bellocchio et al. (2004). Gelatinolytic activity of matrix metalloproteinase 9 (MMP9) was determined by scanning the lysis band in the 72-KD) area. For MPO determination, samples were probed with rabbit polyclonal anti-human MPO Ab (Calbiochem, San Diego, Calif.) and visualized using electrochemiluminescence (ECL) (Amersham Pharmacia Biotech, Piscataway, N.J.).

Indoleamine 2,3-dioxygenase (IDO) was detected by immunoblotting with rabbit polyclonal IDO-specific antibody, as described. Bozza et al. (2005). The positive control consisted of IDO-expressing MC24 transfectants and the negative control was mock-transfected MC22 cells.

Cytokines were quantified by real-time RT-PCR, ELISA and ELISPOT assays, as follows. Real-time RT-PCR was performed using the iCycler iQ® detection system (Bio-Rad, Hercules, Calif.) and SYBR® Green chemistry (Finnzymes Oy, Espoo, Finland). Cells were lysed and total RNA was extracted using RNeasy Mini Kit (QIAGEN S.p.A., Milano, Italy) and was reverse transcribed with Sensiscript Reverse Transcriptase (QIAGEN) according to the manufacturer's directions. PCR primers were obtained from Invitrogen (Carlsbad, Calif.). The PCR primers used were: forward primer, 5'-CACCCTTGCCCTCCTAAACC (SEQ ID NO: 1), and reverse primer, 5'-CAAGGCACAGGGTCATCATC (SEQ ID NO: 2), for mouse IL-12p35; forward primer, 5'-CCAGCAGCTCTCTCGGAATC (SEQ ID NO: 3), and reverse primer 5'-TCATATGTCCCGCTGGTGC (SEQ ID NO: 4), for mouse IL-23p19; forward primer, 5'-CTTCT-TAACAGCACGTCCTGG (SEQ ID NO: 5), and reverse primer 5'-GGTCTCAGATCTCGCAGGTCA (SEQ ID NO: 6), for IL-12Rβ2; forward primer, 5'-TGAAAGAGAC-CCTACATCCCTTGA (SEQ ID NO: 7), and reverse primer 5'-CAGAAAATTGGAAGTTGGGATATGTT (SEQ ID NO: 8), for IL-23R; forward primer, 5'-CGCAAAGACCTGTAT-GCCAAT (SEQ ID NO: 9), and reverse primer, 5'-GGGCT-GTGATCTCCTTCTGC (SEQ ID NO: 10) for mouse γ-actin.

PCR amplification of the housekeeping γ-actin gene was performed for each sample (triplicates) to control for sample loading and allow normalization between samples as per the manufacturer's instructions (Applied Biosystems, Foster City, Calif.). Water controls were included to ensure specificity. The thermal profile for SYBR® Green real time PCR was at 95° C. for 3 min, followed by 40 cycles of denaturation for 15s at 95° C. and an annealing/extension step of 1 min at 60° C. Each data point was examined for integrity by analysis of the amplification plot. The mRNA-normalized data were expressed as relative cytokine mRNA in treated cells compared to that of mock-infected cells. Cytokine content was assessed by enzyme-linked immunosorbent assays (R&D Systems and, for IL-23, eBioscience, Società Italiana Chimici, Rome, Italy) on tissue homogenates or supernatants of cultured cells. The detection limits (pg/ml) of the assays were <16 for IL-12p70, <30 for IL-23, <10 for IFN-γ, <3 for IL-10, <10 for IL-17 and <4,6 for TGF-β1. AID EliSpot assay kits (Amplimedical, Buttigliera Alta, Turin, Italy) were used on purified MLN CD4+ T cells co-cultured with Candida-pulsed DC for 3 days to enumerate cytokine-producing cells.

Statistical analysis of the data was performed as follows. The log-rank test was used for paired data analysis of the Kaplan-Meier survival curves. Student's t-test or analysis of variance (ANOVA) and Bonferroni's test were used to determine the statistical significance of differences in organ clearance and in vitro assays. Significance was defined as p<0.05. The data reported are either from one representative experiment out of three independent experiments or pooled from three to five experiments. The in vivo groups consisted of 6-8 mice/group.

EXAMPLE 4

Role of IL-23/IL-17 in the Susceptibility to Candidiasis

To evaluate the contribution of the IL-23/IL-17 pathway to *C. albicans* infection, we compared p19$^{-/-}$, p35$^{-/-}$, p40$^{-/-}$ and C57BL/6 mice for susceptibility to gastrointestinal infection in terms of survival, fungal growth, and tissue pathology, as well as for parameters of inflammatory and adaptive Th1/Th17 immunity. The results (FIGS. 1A-E) showed that resistance to candidiasis was severely impaired in p35$^{-/-}$ mice, more than 50% of which succumbed to the infection (FIG. 1A) with an elevated fungal growth in the stomach (FIG. 1B). In contrast, the ability to restrict the fungal growth was greatly increased in p19$^{-/-}$ mice as compared to C57BL/6 mice three and ten days after the infection. Notably, p40$^{-/-}$ mice, deficient in both IL-12 and IL-23, were less susceptible than p35$^{-/-}$ mice and more susceptible than p19$^{-/-}$ mice to candidiasis, emphasizing the differential roles of IL-12 for control of *Candida*. Mencacci et al. (1998) *J. Immunol.* 161:6228. Similar results were observed after intravenous infection of p35$^{-/-}$ and p19$^{-/-}$ mice, with a mean survival time (MST) of 6±2 versus 20±3 days (5×10$^5$ fungal cell inoculum), and 4±2 versus 15±3 days (10$^6$ fungal cell inoculum), respectively. Histopathological examination of the stomach revealed the presence of parakeratosis, acanthosis and limited inflammatory reaction in C57BL/6, p19$^{-/-}$ or p40$^{-/-}$ mice, although p40$^{-/-}$, and in particular p19$^{-/-}$ mice, showed infiltrates of mononuclear cells. In contrast, numerous fungal hyphae were present in the keratinized layer in association with a massive infiltrate of PMN, signs of epithelial necrosis and prominent acanthosis in the stomach of p35$^{-/-}$ mice. These results suggest that the IL-23 and IL-12 pathways have divergent roles in candidiasis.

To correlate these findings with IL-12/Th1 and IL-23/Th17 immune responses, mice were assessed for p35, p19, IL-12Rβ2 and IL-23R mRNA expression in MLN one or three days after the infection (FIG. 1C), and frequencies of IFN-γ-, IL-4- or IL-17-producing CD4+ cells in MLN at day seven after infection (FIG. 1D). We found increased levels p35 and IL-12Rβ2, and numbers of IFN-γ+ cells, in p19$^{-/-}$ mice compared to C57BL/6 mice demonstrating augmented IL-12/Th1 responses in the absence of IL-23. In contrast, levels of p19 and IL-23R and number of IL-17-producing cells were enhanced in mice lacking IL-12 (p35$^{-/-}$). Expectedly, the number of IL-4-producing cells was also considerably enhanced in p35$^{-/-}$ mice. These data demonstrate a predominant Th1 response promoted by IL-12 and limited by IL-23 in wild-type C57BL/6 mice. IL-12 suppresses IL-23 and IL-17 production, and vice versa—IL-23 inhibits IL-12 and IFN-γ, production—indicating cross-regulation of IL-23/Th17 and IL-12/Th1 pathways. These data suggest that an elevated IL-23/Th17 response renders mice highly susceptible to candidiasis.

EXAMPLE 5

Role of IL-23/IL-17 in the Susceptibility to Aspergillosis

To determine whether, similar to candidiasis, the activation of the IL-23/IL-17 pathway correlates with susceptibility to aspergillosis, p19$^{-/-}$, p35$^{-/-}$, p40$^{-/-}$ or C57BL/6 mice were assessed for susceptibility to pulmonary aspergillosis and parameters of inflammatory and adaptive Th1/Th17 immunity. The results (FIG. 2A) show that the fungal burden was reduced in p35$^{-/-}$ mice, and to an even greater extent in p19$^{-/-}$ mice, suggesting that IL-12, and especially IL-23, inhibit control of (i.e. promote) *Aspergillus* infection. Histopathological examination of the lung revealed the presence of a mild inflammatory pathology in C57BL/6, p40$^{-/-}$ or p19$^{-/-}$ mice, characterized by few infiltrates of inflammatory mononuclear cells scattered in an otherwise intact lung parenchyma. Although the number of infiltrating mononuclear cells was higher in p19$^{-/-}$ mice, no signs of parenchyma destruction were observed. In contrast, a massive infiltration of PMN (about 8-10 fold increase of Gr1+CD11c-PMN) was present in the lungs of p35$^{-/-}$ mice associated with signs of extensive interstitial pneumonia. Similar to infection with *Candida*, expression of IL-12 and IL-23 and their respective receptors were crossregulated, with upregulation of p35 and IL-12Rβ2 in TLN of p19$^{-/-}$ mice, and upregulation of p19 and IL-23R in TLN of p35$^{-/-}$ mice, compared to C57BL/6 mice (FIG. 2B). In contrast, absence of both IL-12 and IL-23 in p40$^{-/-}$ mice did not significantly alter expression of p35 and p19 or their receptors IL-12Rβ2 and IL-23R. Moreover, number of IFN-γ+ and IL-17+ producing CD4+ T cells was increased in p19$^{-/-}$ and p35$^{-/-}$ mice, respectively, at day 7 after infection (data not shown). In the lung, the levels of IL-12p70 were much higher in p19$^{-/-}$ (554±44 pg/ml) than in C57BL/6 mice (68±8 pg/ml), and IL-23 could be detected only in p35$^{-/-}$ mice (79±11). IL-17 was increased in p35$^{-/-}$ mice (246±17 pg/ml) compared to C57BL/6 mice (37±7 pg/ml). These data suggest that a heightened IL-23/IL-17-dependent inflammatory response is also associated with susceptibility to aspergillosis.

EXAMPLE 6

Role of TGF-β in IL-23/IL-17-Mediated Susceptibility to Fungal Infection

To study the role of IL-17 in susceptibility to fungal infections, we treated mice with an anti-IL-17 neutralizing antibody shortly after fungal infection. Blockade of IL-17 greatly increased resistance to both *C. albicans* and *A. fumigatus*, as judged by a decreased fungal growth (FIG. 3A), tissue inflammation and PMN infiltration (data not shown) in the relevant target organs. Resistance was associated with an increased frequency of IFN-γ+ Th1 cells and a decreased frequency of Th17 cells, resulting in reduced amounts of IL-17 secreted by MLN cells (FIG. 3B). Similarly, neutralization of IL-23 by antibody increased resistance to fungal infection and Th1 development and confirm our data obtained in p19$^{-/-}$ mice (FIG. 3B). These results clearly demonstrate that the IL-23/IL-17 pathway confers susceptibility to fungal infection by inhibition of protective Th1 immunity.

Recent results suggest that TGF-β together with IL-6 promotes Th17 development. Bettelli and Kuchroo (2005)*J. Exp. Med.* 201:169; Mangan et al. (2006) *Nature* 441:231; Veldhoen et al. (2006) *Immunity* 24:179. We assessed the effect of TGF-β on Th cell development and fungal control in mice by treatment with TGF-β-neutralizing antibody. Notably, TGF-β inhibition did not affect development of IL-17 producing cells during both *C. albicans* and *A. fumigatus* infection (FIG. 3B), and a slight but significant reduction in fungal burden was observed only in mice with *Aspergillus* but not with *Candida* (FIG. 3A) but in neither infection was activation of CD4+Th17 cells affected by treatment. Because TGF-β neutralization effectively reduced TGF-β production in infections (from 46 to 24 pg/ml in the stomach and from 36 to 15 pg/ml in the lung), we conclude that TGF-β plays a minor role in Th17-mediated susceptibility to fungal infection.

EXAMPLE 7

Role of IL-23/IL-17 in Fungal Infection in the Absence of IL-12

The above data would suggest that one possible mechanism through which the IL-23/IL-17 axis determines susceptibility to fungal infections relies on the relative ability to restrain protective Th1 responses. To formally prove it, blockade of IL-23 was done under conditions of either heightened (IL-4$^{-/-}$ mice) or deficient (IFN-γ$^{-/-}$ mice) Th1 reactivity. Mice were intragastrically infected with *C. albicans* and subjected to IL-23 blockade by means of neutralizing antibodies. Consistent with prior publications (Romani et al. (1992) *J. Exp. Med.* 176:19; Cenci et al. (1998) *J. Immunol.* 161:3543), the fungal load was lower in IL-4$^{-/-}$ and higher in IFN-γ$^{-/-}$ mice compared to BALB/c mice, demonstrating the importance of IFN-γ for control of infection. Similar to WT mice, blockade of IL-23 greatly decreased the fungal burden in the stomach of IL-4$^{-/-}$ mice (FIG. 3C) and concomitantly increased the IL-12p70/IFN-γ production in MLN (data not shown), suggesting that both the Th2 and IL-23/Th17 pathway additively antagonize protective antifungal responses. Surprisingly, the elevated fungal burden in IFN-γ$^{-/-}$ mice was further increased upon neutralization of IL-23 (FIG. 3C), which resulted in decreased IL-23 production (229 versus 21 pg/ml) IL-17 production (279 versus 95 pg/ml) in anti-IL-23 treated mice. Thus, IL-23 can have a protective role in fungal infection in the absence of IFN-γ. However, IL-23 has the opposite effect in the absence of IL-12p70, or in the absence of both IL-12p70 and IFN-γ, as demonstrated by reduced fungal burden upon neutralization of IL-23 in p35$^{-/-}$ or doubly deficient IFN-γ$^{-/-}$/p35$^{-/-}$ mice (FIG. 3C). These data suggest that the protective role of IL-23 in the absence of IFN-γ is mediated by IL-12p70. Notably, a moderate protective role of TL-23 in the absence of IL-12p70 was also observed in tuberculosis, where IL-23 partially replaced IL-12p70 in the induction of protective IFN-γ-producing CD4+ T cells. Khader et al. (2005).

EXAMPLE 8

Production of IL-23 and IL-12 in Dendritic Cells in Response to Fungal Infection It has already been shown that IL-23 is produced by human DC in response to *Aspergillus* in vitro. Gafa et al. (2006) *Infect. Immun.* 74:1480. We evaluated here whether IL-23 is produced by DC in response to *C. albicans* and how it relates to the production of IL-12 and IL-10, two cytokines essentially required for the induction of protective tolerance to the fungus. Romani & Puccetti (2006).

For this purpose, we generated bone marrow derived DCs in the presence of either GM-CSF (GM-DC) or Flt3-L (FL-DC), which share characteristics of myeloid DC and plasmacytoid DC, respectively. Although FL-DC encompasses populations equivalent to mixtures of freshly harvested splenic CD8+, CD8- and B220+LyC6+ plasmacytoid DC (Naik et al. (2005) *J. Immunol.* 174:6592), we have recently demonstrated that the functional activity of FL-DC resides in plasmacytoid DC or in the combination of CD8- and CD8+ DC. Romani et al. (2006) *Blood* 108:2265. DC were stimulated in vitro with yeasts or hyphae of the fungus and assessed for cytokine mRNA expression and production. Zymosan and LPS were used as positive controls of GM-DC and CpG-ODN as a positive control of FL-DC.

The results showed a dichotomy in the cytokine expression and production by the two subsets of DC subsets in response to the fungus. RT-PCR analysis revealed that p19 mRNA expression only increased in GM-DC in response to yeasts more than hyphae; p35 mRNA expression slightly increased in GM-DC in response to yeasts but, similar to IL-10, greatly increased in FL-DC exposed to hyphae (FIG. 4A). The measurement of actual cytokine production in culture supernatants confirmed that IL-23 was produced by GM-DC in response to yeasts, particularly at high fungus:DC ratios, as well as to zymosan or LPS (FIG. 4B). The maximum level of IL-23 production was observed at 12 h of incubation (FIG. 4B), and declined thereafter (data not shown). Conversely, both IL-12p70 and IL-10 were mainly produced by FL-DC stimulated with *Candida* hyphae, LPS or CpG-ODN for 12 h (FIG. 4B) and continued to be elevated thereafter (data not shown). Together, these data suggest that IL-23 is produced by myeloid DC in response to the fungus, particularly in condition of high level fungal growth and earlier than other directive cytokines. The ability of distinct DC subsets to produce directive cytokines in response to *Candida* may thus condition their antifungal immunity in vivo. As a matter of fact, as already shown for *Aspergillus* (Romani et al. (2006) *Blood* 108:2265), *Candida*-pulsed FL-DC conferred protection and *Candida*-pulsed GM-DC exacerbated the infection upon adoptive transfer into recipient mice with candidiasis.

EXAMPLE 9

Cross-Regulation of IL-23 and IL-12

To verify whether IL-12p70 and IL-23 production are cross-regulated in response to the fungus, we measured 1'-12p70 and IL-23 secretion by splenic DC from p19$^{-/-}$, p35$^{-/-}$ and C57BL/6 control mice after exposure to either IL-12p70 or IL-23, or the corresponding neutralizing antibodies. FIG. 4C shows that IL-12p70 and IL-23 are indeed cross-regulated as the production of IL-12p70 was higher in p19$^{-/-}$ DC and that of IL-23 higher in p35$^{-/-}$ DC as compared to WT DC. Moreover, the exposure to either IL-12p70 or IL-23 significantly decreased IL-23 or IL-12p70 secretion, respectively, by WT DC and the reverse was true in condition of IL-12 or IL-23 neutralization (FIG. 4D). Because RT-PCR revealed that unstimulated DC express both cytokine receptors (data not shown), these data suggest the existence of a paracrine loop by which IL-12p70 and IL-23 production by DC is reciprocally regulated.

EXAMPLE 10

Role of TLR in IL-23 Production by Dendritic Cells

To define the possible TLR-dependency of IL-23 production in response to fungi, we measured IL-23 production in response to yeasts or conidia by GM-DC generated from TLR-2$^{-/-}$ or TLR-4$^{-/-}$ mice as well as from MyD88$^{-/-}$ and TRIF$^{-/-}$ mice. Akira and Takeda (2004) *Nat. Rev. Immunol.* 4:499. FIG. 5A shows that both TLR2 and TLR4 are essential for IL-23 production by signaling through MyD88, but not TRIF. Notably, IL-23 appeared to be promoted even in the absence of the TRIF. Therefore, IL-23 is produced by conventional DC in response to fungi through the TLR/MyD88-dependent inflammatory pathway.

To define whether T cells may also regulate IL-23 production, we assessed levels of IL-23 produced in supernatants of DC cultured with CD4+ T cells. The results clearly showed that IL-23 production was-up-regulated in cultures of T cells stimulated with *Candida* pulsed-DC from C57BL/6 and particularly p35$^{-/-}$ mice (group 3 vs group 6, FIG. 5B), a finding suggesting that activated T cells may provide a positive feedback loop for amplification of IL-23 production. In addition, the results of criss-cross experiments confirmed that IL-23-producing DC were necessary and sufficient to activate IL-17-producing cells (groups 7 and 8). Furthermore, neutralization of IL-23 by mAb added to co-cultures of DC and T cells inhibited IL-17 production (group 4 versus group 5, FIG. 5C), whereas TGF-β neutralization affected IFN-γ (group 1 versus group 3) but not IL-17 production (group 4 versus group 6).

EXAMPLE 11

Effect of IL-23 and IL-17 on Antifungal Effector Functions of Polymorphonuclear Neutrophils PMN are essential in the initiation and execution of the acute inflammatory response to fungi. Romani (2004). The finding that PMN were abundantly recruited to sites of infections, together with early fungal growth in p35$^{-/-}$ mice, led us to hypothesize that the IL-23/IL-17-dependent pathway could adversely affect the anti-fungal effector functions of PMN. We evaluated therefore the fungicidal activity of PMN from either p19$^{-/-}$ or p35$^{-/-}$ mice, and from WT mice cultured with recombinant IL-23 or IL-17 in the absence or presence of IFN-γ. The killing activity was significantly increased in p19$^{-/-}$ PMN and decreased in p35$^{-/-}$ mice as compared to C57BL/6 PMN (FIG. 6A). Before exposing PMN to these cytokines, we verified whether, similar to IL-17R (Yao et al. (1995) *Immunity* 3:811-821), IL-23R was also expressed on murine PMN. Quantitative RT-PCR revealed that unstimulated PMN express IL-23R, whose expression was further increased after stimulation with LPS (data not shown), a finding suggesting that PMN are also responsive to IL-23.

Exposure to either cytokine impaired the killing activity of WT PMN in a dose-dependent manner (FIG. 6B) in the absence and presence of IFN-γ (FIG. 6C). Therefore, IL-23 and EL-17 negatively regulated the antifungal effector functions of PMN, which may account for the failure of p35$^{-/-}$ mice to efficiently restrict fungal growth. Thus, although IL-17 is a potent chemoattractant for PMN (Ye et al. (2001) *J. Exp. Med.* 194:519) such that decreased influx of peripheral PMN to infected organs accounted for the high susceptibility of IL-17AR-deficient mice to candidiasis (Huang et al. (2004) *J. Infect. Dis.* 190:624), our results also point to a detrimental effect for IL-17 on PMN function.

EXAMPLE 12

Effect of IL-23 and IL-17 on IDO-Dependent Anti-inflammatory Program of Polymorphonuclear Neutrophils We have already shown that IFN-γ-mediated IDO activation negatively regulates the inflammatory program of PMN against *Candida*, such that IDO blockade resulted in the promotion of an inflammatory state of PMN. Bozza et al. (2005). MMP-9 and MPO are typical inflammatory markers that have been proposed to be activated by IL-17. Kolls and Linden (2004) *Immunity* 21:467. Therefore we evaluated the effects of both IL-23 and IL-17 on *C. albicans* induced MMP-9, MPO and IFN-γ-mediated IDO production. Both IL-23 and, in particular, IL-17 increased MMP-9 and MPO considerably (FIG. 6D). IDO expression and inflammatory response of WT PMN. In contrast, both cytokines completely antagonized the induction of IDO by IFN-γ (FIG. 6E). Interestingly, the number of apoptotic PMN was significantly decreased upon the exposure to both IL-23 and IL-17 (data not shown), suggesting that these cytokines also enhance PMN viability. This could be a further mechanism by which inflammation is perpetuated by the Th17 pathway. Therefore, the ability to subvert the inflammatory program of PMN along with the increased net proteolytic load in inflamed tissues may account for the inflammatory pathology associated with Th17 cell activation in fungal infections.

EXAMPLE 13

Assay for IL-23-Specific Antagonists Based on IL-17 Production

In vitro studies using murine draining lymph node (DLN) cells have demonstrated that eliminating IL-23 inhibits or eliminates IL-17 producing cells, while adding IL-23 generates or stimulates IL-17 secretion, as determined by fluorescence activated cell sorting (FACS®) analysis. See WO 2004/071517, Langrish et al. (2005) *J. Exp. Med.* 201:233. See also Aggarwal et al. (2003) *J. Biol. Chem.* 278:1910. In these experiments, DLN cells were treated with cytokine or antibodies for 5 days. Cells were isolated from antigen-primed normal wild type mice, and cultured in the presence of either rIL-12 or rIL-23. Analysis of the CD4$^+$ T cells in the DLN cultures demonstrated that IL-12 promoted the development of IFN-γ producing cells, with loss of the IL-17 producing population. In contrast, IL-23 promoted the development of IL-17 producing cells, with loss of the IFN-γ producing population. Anti-p19 antibodies reduced IL-17 production but did not affect IFN-γ levels, whereas anti-p35 antibodies did not change IL-17 production. Taken together these results showed that IL-23 selectively promotes the development of IL-17 producing CD4$^+$ T cells.

This difference in the biological activities of IL-23 and IL-12 is used to assess the potency and specificity of potential IL-23 antagonists, relative to IL-12, as follows.

The baseline data on IL-23 and IL-12 activity in the absence of a potential IL-23-specific antagonist are obtained as follows. Normal wild type SJL mice are immunized (s.c.) with proteolipid peptide (PLP) emulsified in complete Freund's adjuvant, and with (i.v.) pertussis toxin. Draining lymph nodes are removed at day 9 post-immunization, and mononuclear cells are either assessed for intracellular IFN-γ and IL-17 production right away (as described below), or isolated and cultured in the presence of PLP plus either rIL-12 or rIL-23 for 5 days. Cells are stimulated for 3 hours with PMA (50 ng/ml)/ionomycin (500 ng/ml) in the presence of Golgi-plug for 4 h, then surface stained for CD4, permeabilized, and intracellular stained for IFN-γ and IL-17. Flow cytometry plots are gated on alive CD4$^+$ T cells.

The effects of IL-23 and IL-12 are evaluated relative to the control cells that were not cytokine treated. Typically, IL-23 treated cells will exhibit an increased percentage of IL-17 producing cells with no increase in IFN-γ producing cells, whereas IL-12 treated cells will exhibit an increased percentage of IFN-γ producing cells with no increase (or even a decrease) in IL-12 producing cells.

The potency and specificity of a potential IL-23-specific antagonist is determined by performing the same experiment in the presence of the antagonist, or preferably at a series of concentrations of antagonist. An IL-23 specific antagonist will inhibit the activity of IL-23 (i.e. the antagonist will decrease the percentage of EL-17 producing cells that would otherwise be induced by IL-23), but not substantially reduce the activity of IL-12. An agent that inhibits the activity of IL-12 or both IL-12 and IL-23 is not an IL-23-specific antagonist.

Optionally, a positive control may be included in which a known anti-p19 antagonist antibody is used to specifically inhibit the activity of IL-23.

EXAMPLE 14

Mycobacterial Infections

A method of demonstrating the efficacy of the compositions and methods of the present invention in the treatment of mycobacterial infections is provided. C57BL/6 mice are infected with mycobacteria as follows. Theracys-BCG Live (Aventis Pasteur, Inc., Swiftwater, Pa.), a freeze-dried preparation of the Connaught strain of *Bacille Calmette* and *Guerin* and attenuated strain of *M. bovis*, is reconstituted as recommended by the manufacturer. The reconstituted bacteria are brought to a concentration of approximately $6 \times 10^7$ cfu/mL in 10% glycerol saline. Aliquots are diluted to appropriate concentration in 0.02% Tween-80/0.9% saline prior to injection into mice.

Six to eight week old female C57BL/6 mice are infected intravenously via the lateral tail vein with approximately $3.5 \times 10^5$ cfu of BCG. Mice are given 1 mg of the appropriate monoclonal antibody (e.g. isotype control, anti IL-23p19, or anti IL-23R) in 0.9% saline, administered subcutaneously, one day prior to mycobacteria infection and again 1-2 weeks post mycobacteria infection. Mice are sacrificed at appropriate time points after infection by $CO_2$ narcosis.

The sacrificed BCG infected mice are analyzed as follows. Blood is purged from the lungs by perfusing RPMI 1640 through the right ventricle of the heart after the inferior vena cava is severed. The left lung, the lower right liver lobe, and half the spleen are aseptically removed. The tissues are homogenized in 0.9% NaCl/0.02% Tween 80 with a Mini-Bead Beater-8 homogenizer (BioSpec Products, Bartlesville, Okla.). Viable mycobacteria are quantitated by plating 10-fold serial dilutions of organ homogenates onto 7H10 Middlebrook agar plates (Becton Dickinson, Sparks, Md.). Colony-forming units (CFU) are manually counted after two weeks of incubation at 37° C. A statistically significant decrease in bacterial burden (as measured by CFU) in animals treated with anti-IL-23 antibodies (e.g. anti-IL-23p19 antibodies or anti-IL-23R antibodies) as compared with control mice (e.g. isotype control) is evidence of efficacious treatment of mycobacterial infection.

What is claimed is:

1. A method of enhancing a Th1 immune response in a subject having a chronic fungal infection selected from the group consisting of candidiasis and aspergillosis, comprising administering an antagonist of IL-23.

2. The method of claim 1 wherein the enhanced Th1 immune response comprises a 2-fold or greater increase in the percentage of CD4$^+$ T cells expressing IFN-γ compared with the percentage of CD4$^+$ T cells expressing IFN-γ prior to administering said antagonist of IL-23.

3. The method of claim 1 wherein the enhanced Th1 immune response comprises a 2-fold or greater decrease in the percentage of CD4$^+$ T cells expressing IL-17 compared with the percentage of CD4$^+$ T cells expressing IL-17 prior to administering said antagonist of IL-23.

4. The method of claim 1, wherein the antagonist of IL-23 is a binding compound that binds to IL-23p19.

5. The method of claim 1, wherein the antagonist of IL-23 is a binding compound that binds to IL-23R.

6. The method of claim 4 wherein the binding compound is an antibody or antigen binding fragment thereof.

7. The method of claim 5 wherein the binding compound is an antibody or antigen binding fragment thereof.

8. The method of claim 4 wherein the binding compound is an antibody fragment selected from the group consisting of Fab, Fab', Fab'-SH, Fv, scFv, F(ab')$_2$, a single chain antibody, and a diabody.

9. The method of claim 5 wherein the binding compound is an antibody fragment selected from the group consisting of Fab, Fab', Fab'-SH, Fv, scFv, F(ab')$_2$, a single chain antibody, and a diabody.

10. The method of claim 6 wherein the antibody is a humanized or fully human antibody or antigen binding fragment thereof.

11. The method of claim 7 wherein the antibody is a humanized or fully human antibody or antigen binding fragment thereof.

12. The method of any of the preceding claim 1 further comprising administering at least one of an antagonist of IL-17A, IL-6 or TGF-β.

* * * * *

UNITED STATES PATENT AND TRADEMARK OFFICE
CERTIFICATE OF CORRECTION

PATENT NO.        : 8,586,035 B2  
APPLICATION NO.   : 12/525003  
DATED             : November 19, 2013  
INVENTOR(S)       : Kopf et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 941 days.

Signed and Sealed this
Twenty-second Day of September, 2015

Michelle K. Lee
*Director of the United States Patent and Trademark Office*